US011779243B2

(12) United States Patent
Li et al.

(10) Patent No.: US 11,779,243 B2
(45) Date of Patent: Oct. 10, 2023

(54) CUSTOMIZED ALIGNER CHANGE INDICATOR

(71) Applicant: Align Technology, Inc., San Jose, CA (US)

(72) Inventors: Huizhong Li, San Jose, CA (US);
Andrew Jang, San Mateo, CA (US);
Michael Christopher Cole, Longmont, CO (US); Yuxiang Wang, Newark, CA (US); Jun Sato, San Jose, CA (US);
Allen R. Boronkay, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 43 days.

(21) Appl. No.: 16/730,870

(22) Filed: Dec. 30, 2019

(65) Prior Publication Data
US 2020/0214598 A1 Jul. 9, 2020

Related U.S. Application Data

(60) Provisional application No. 62/789,369, filed on Jan. 7, 2019.

(51) Int. Cl.
A61B 5/11 (2006.01)
A61C 7/08 (2006.01)
(Continued)

(52) U.S. Cl.
CPC .......... *A61B 5/1111* (2013.01); *A61B 5/0022* (2013.01); *A61C 7/002* (2013.01);
(Continued)

(58) Field of Classification Search
CPC ................ A61B 5/1111; A61B 5/0022; A61B 2562/0261; A61C 7/002; A61C 7/08;
(Continued)

(56) References Cited

U.S. PATENT DOCUMENTS 2,467,432 A 4/1949 Kesling
3,407,500 A 10/1968 Kesling
(Continued)

FOREIGN PATENT DOCUMENTS

AU 3031677 A 5/1979
AU 517102 B2 7/1981
(Continued)

OTHER PUBLICATIONS

AADR. American Association for Dental Research, Summary of Activities, Mar. 20-23, 1980, Los Angeles, CA, p. 195.
(Continued)

Primary Examiner — Patrick Fernandes
(74) Attorney, Agent, or Firm — Wilson Sonsini Goodrich & Rosati

(57) ABSTRACT

According to the techniques herein, one or more sensors coupled to an aligner are used to sense one or more physical qualities of the aligner to determine whether the physical qualities indicate that the aligner material has relaxed and has, e.g., reduced the force systems applied to teeth and/or that the teeth movement for the stage has slowed down. The sensors may provide a signal that represents whether or not the physical qualities fall below a threshold value. A treatment plan may be modified if needed. These techniques have the potential to make treatment plans faster and more effective by speeding up some stages while making sure some, perhaps other, stages are implemented only after the teeth are near the appropriate position.

20 Claims, 14 Drawing Sheets

(51) Int. Cl.
 *A61C 7/00*   (2006.01)
 *G01B 7/16*   (2006.01)
 *A61B 5/00*   (2006.01)

(52) U.S. Cl.
 CPC .................. *A61C 7/08* (2013.01); *G01B 7/18* (2013.01); *G01B 7/22* (2013.01); *A61B 2562/0261* (2013.01)

(58) Field of Classification Search
 CPC . A61C 19/04; G01B 7/18; G01B 7/22; G16H 20/40
 See application file for complete search history.

(56) References Cited

U.S. PATENT DOCUMENTS

| | | |
|---|---|---|
| 3,600,808 A | 8/1971 | Reeve et al. |
| 3,660,900 A | 5/1972 | Andrews et al. |
| 3,683,502 A | 8/1972 | Wallshein et al. |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling et al. |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut et al. |
| 4,500,294 A | 2/1985 | Lewis et al. |
| 4,504,225 A | 3/1985 | Yoshii |
| 4,505,673 A | 3/1985 | Yoshii et al. |
| 4,526,540 A | 7/1985 | Dellinger et al. |
| 4,575,330 A | 3/1986 | Hull et al. |
| 4,575,805 A | 3/1986 | Moermann et al. |
| 4,591,341 A | 5/1986 | Andrews et al. |
| 4,609,349 A | 9/1986 | Cain et al. |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling et al. |
| 4,676,747 A | 6/1987 | Kesling et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz et al. |
| 4,798,534 A | 1/1989 | Breads et al. |
| 4,836,778 A | 6/1989 | Baumrind et al. |
| 4,837,732 A | 6/1989 | Brandestini et al. |
| 4,850,864 A | 7/1989 | Diamond et al. |
| 4,850,865 A | 7/1989 | Napolitano et al. |
| 4,856,991 A | 8/1989 | Breads et al. |
| 4,877,398 A | 10/1989 | Kesling et al. |
| 4,880,380 A | 11/1989 | Martz et al. |
| 4,889,238 A | 12/1989 | Batchelor et al. |
| 4,890,608 A | 1/1990 | Steer et al. |
| 4,935,635 A | 6/1990 | O'Harra et al. |
| 4,936,862 A | 6/1990 | Walker et al. |
| 4,937,928 A | 7/1990 | Van et al. |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell et al. |
| 5,011,405 A | 4/1991 | Lemchen |
| 5,017,133 A | 5/1991 | Miura et al. |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman et al. |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson et al. |
| 5,342,202 A | 8/1994 | Deshayes et al. |
| 5,368,478 A | 11/1994 | Andreiko et al. |
| 5,382,164 A | 1/1995 | Stern et al. |
| 5,395,238 A | 3/1995 | Andreiko et al. |
| 5,431,562 A | 7/1995 | Andreiko et al. |
| 5,440,326 A | 8/1995 | Quinn et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern et al. |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. et al. |
| 5,621,648 A | 4/1997 | Crump et al. |
| 5,645,420 A | 7/1997 | Bergersen et al. |
| 5,645,421 A | 7/1997 | Slootsky et al. |
| 5,655,653 A | 8/1997 | Chester et al. |
| 5,683,243 A | 11/1997 | Andreiko et al. |
| 5,692,894 A | 12/1997 | Schwartz et al. |
| 5,725,376 A | 3/1998 | Poirier et al. |
| 5,725,378 A | 3/1998 | Wang et al. |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson et al. |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump et al. |
| 5,880,962 A | 3/1999 | Andersson et al. |
| 5,934,288 A | 8/1999 | Avila et al. |
| 5,957,686 A | 9/1999 | Anthony et al. |
| 5,964,587 A | 10/1999 | Sato et al. |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda et al. |
| 6,049,743 A | 4/2000 | Baba et al. |
| 6,062,861 A | 5/2000 | Andersson |
| 6,068,482 A | 5/2000 | Snow et al. |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,206,835 B1 * | 3/2001 | Spillman, Jr. ........ A61B 5/0215 128/903 |
| 6,217,325 B1 | 4/2001 | Chishti et al. |
| 6,217,334 B1 | 4/2001 | Hultgren et al. |
| 6,244,861 B1 | 6/2001 | Andreiko et al. |
| 6,309,215 B1 | 10/2001 | Phan et al. |

(56) References Cited

U.S. PATENT DOCUMENTS

| | | |
|---|---|---|
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier et al. |
| 6,398,548 B1 | 6/2002 | Muhammad et al. |
| 6,402,707 B1 | 6/2002 | Ernst et al. |
| 6,450,807 B1 | 9/2002 | Chishti et al. |
| 6,482,298 B1 | 11/2002 | Bhatnagar et al. |
| 6,524,101 B1 | 2/2003 | Phan et al. |
| 6,554,611 B2 | 4/2003 | Shishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 6,749,614 B2 | 6/2004 | Teitelbaum et al. |
| 6,830,450 B2 | 12/2004 | Knopp et al. |
| 7,892,474 B2 | 2/2011 | Shkolnik et al. |
| 9,205,601 B2 | 12/2015 | Desimone et al. |
| 9,211,678 B2 | 12/2015 | Desimone et al. |
| 9,216,546 B2 | 12/2015 | Desimone et al. |
| 9,321,215 B2 | 4/2016 | Dudley |
| 9,511,543 B2 | 12/2016 | Tyler |
| 9,655,693 B2 | 5/2017 | Li et al. |
| 2002/0006597 A1 | 1/2002 | Andreiko et al. |
| 2003/0009252 A1 | 1/2003 | Pavlovskaia et al. |
| 2003/0139834 A1 | 7/2003 | Nikolskiy et al. |
| 2003/0224311 A1 | 12/2003 | Cronauer et al. |
| 2004/0128010 A1 | 7/2004 | Pavlovskaia et al. |
| 2005/0055118 A1 | 3/2005 | Nikolskiy et al. |
| 2007/0154895 A1* | 7/2007 | Spaid ............... G01N 33/54366 435/7.1 |
| 2008/0149294 A1* | 6/2008 | Frasier ................ B29C 64/165 164/256 |
| 2013/0243655 A1* | 9/2013 | Li ..................... B01L 3/502707 422/82.05 |
| 2018/0000565 A1* | 1/2018 | Shanjani ................ A61C 19/04 |
| 2019/0338067 A1 | 11/2019 | Liska et al. |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-2019213588 A1 | 11/2019 |

OTHER PUBLICATIONS

Alcaniz, et al., "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004.

Bourke, "Coordinate System Transformation," (Jun. 1996), p. 1, retrieved from the Internet Nov. 5, 2004, URL< http://astronomy.swin.edu.au/-pbourke/prolection/coords>.

Boyd et al., "Three Dimensional Diagnosis and Orthodontic Treatment of Complex Malocclusions With the Invisalign Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

(56) References Cited

OTHER PUBLICATIONS

Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on The Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision,"Part 3 The Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
DENT-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClear™ product information, Allesee Orthodontic Appliances—Pro Lab, 1 page (1997).
Duret et al., "CAD/CAM Imaging in Dentistry," Curr. Opin. Dent., 1:150-154 (1991).
Duret et al., "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et al., "Automated Finite Element Modeling of a Human Mandible with Dental Implants," JS WSCG '98—Conference Program, retrieved from the Internet:<http://wscg.zcu.cz/wscg98/papers98/Strasser 98.pdf, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
GIM-ALLDENT Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management,"J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxillofacial Surgery," AAOMS, 3 pages total, (Sep. 13, 1990).
Guess et al., "Computer Treatment Estimates In Orthodontics and Orthognathic Surgery," JCO, pp. 262-28 (Apr. 1989).
Heaven et al., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informationen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System. Allesee Orthodontic Appliances—Pro Lab. 1 page (1998).
JCO Interviews, "Craig Andreiko , DDS, MS on the Elan and Orthos Systems," JCO, pp. 459-468 (Aug. 1994).
JCO Interviews, "Dr. Homer W. Phillips on Computers in Orthodontic Practice, Part 2," JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports On Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).

(56) References Cited

OTHER PUBLICATIONS

Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Li et al.:Soft capacitive tactile sensing arrays fabricated via direct filament casting. Smart Mater. Struct. 25: 075009. 10 pp. (2016).
Manetti, et al., "Computer-Aided Cefalometry and New Mechanics in Orthodontics," (Article Summary in English, article in German), Fortschr Kieferorthop. 44, 370-376 (Nr. 5), 1983.
Mccann, "Inside the ADA," J. Amer. Dent. Assoc., 118:286-294 (Mar. 1989).
Mcnamara et al., "Invisible Retainers," J. Clin. Orthod., pp. 570-578 (Aug. 1985).
Mcnamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording The Dental Cast In Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System In Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolaryngol Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee Orthodontic Appliances—Pro Lab product information, 6 pages (2003).
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml, 5 pages (May 19, 2003).
The Choice is Clear: Red, White & Blue . . . The Simple, Affordable, No-Braces Treatment, Allesee HJ Orthodontic Appliances—Pro Lab product information for patients, (http://ormco.com/aoa/appliancesservices/RWB/patients.html), 2 pages (May 19, 2003).
The Red, White & Blue Way to Improve Your Smile!, Allesee Orthodontic Appliances—Pro Lab product information for patients, 2 pages (1992).
Truax L., "Truax Clasp-Less(TM) Appliance System," Funct. Orthod., 9(5):22-4, 26-8 (Sep.-Oct. 1992).

(56) References Cited

OTHER PUBLICATIONS

Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering Of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 388-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL(http://wscg.zcu.cz/wscg98/wscg98.h).
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be A Candidate For This Invisible No-Braces Treatment, Allesee Orthodontic Appliances—Pro Lab product information for patients, 2 pages (2002).

\* cited by examiner

CUSTOMIZED ALIGNER CHANGE INDICATOR

CROSS-REFERENCE

This application claims the benefit of U.S. Provisional Application No. 62/789,369, filed Jan. 7, 2019, which application is incorporated herein by reference.

TECHNICAL FIELD

The present disclosure is related generally to the technical field of orthodontics. In particular, the present disclosure is related to methods for monitoring material properties of a dental appliance used to implement a treatment plan, and for determining whether nor not to modify a treatment schedule based on those material properties.

BACKGROUND

Orthodontic treatments involve repositioning misaligned teeth and improving bite configurations for improved cosmetic appearance and dental function. Repositioning is accomplished by applying gentle controlled forces to the teeth over an extended period of time. Due to the limited space within the oral cavity and extensive movements that some teeth may undergo, the teeth will often be moved through application of a series of intermediate dental appliance patterns to properly arrange the teeth.

Orthodontic treatments may prescribe removable and/or polymeric repositioning appliance(s) that implement stage(s) of a treatment plan. Each repositioning appliance may be used for a set interval of time and may initially be misaligned with the patient's teeth at the beginning of its stage. The initial misalignment may provide forces to the teeth at various points of contact. The magnitude of repositioning forces exerted by an aligner may depend on the extent of the misalignment. As the teeth gradually move into the desired configuration of a stage, the misalignment may decrease and the applied force may correspondingly lessen.

As the forces applied by an aligner lessen (e.g., as teeth get closer to a target configuration of a stage), the efficacy of the aligner similarly decreases. As an example, once the forces applied by an aligner decrease past certain force(s) prescribed by a treatment plan, the aligner is not as effective as it initially was. To effectively implement the treatment plan, a patient may progress to the next stage in the treatment plan, by, e.g., using the next aligner corresponding to the next stage.

Conventionally, the determination of when to advance a patient to a next stage in a treatment plan was based various factors, such as the prescription of an orthodontic practitioner and/or a treatment schedule that prescribes a specified time interval (e.g., a week or two weeks). However, due to individual variance in tooth movement rates, an actual patient's teeth may not move as prescribed. Under conventional techniques it may be difficult to determine if the rate of movement of an individual patient's teeth accords (or, alternatively, is too high or too low) with the scheduled treatment plan.

SUMMARY

A method for sensing tooth movement or force is disclosed. The method may include sensing a physical quality of a region of a first aligner, the first aligner used to move one or more teeth in accordance with a first stage of a treatment plan, identifying a value for the physical quality based on the sensing, making a first determination whether the value of the physical quality is less than a threshold value, the threshold value corresponding to a specified reduction in a force to teeth applied in accordance with the first stage of the treatment plan, and providing a signal representative of the first determination.

In some embodiments, the physical quality corresponds to a material stress or a material strain of a material of the first aligner. In some embodiments, the signal comprises an electrical signal. In some embodiments, the sensing the physical quality of the region of the first aligner is executed by a sensor coupled to the region of the first aligner.

In some embodiments, the sensor comprises an embedded stress sensor embedded into the region of the first aligner, the embedded stress sensor being configured to sense a movement of the region of the first aligner and to provide a change in electrical conductivity based on the sensed movement. The sensor may include one or more microfluidic channels configured to sense a capacitance of the region of the first aligner and to identify a spatially distributed strain on the region of the first aligner based on the sensed capacitance. In some embodiments, the sensor comprises a plurality of legs configured to sense a distance therebetween and to identify a spatially distributed strain on the region of the first aligner based on the sensed distance.

The threshold value may be associated with a relaxation of a first aligner material of the first aligner beyond a relaxation threshold. The first aligner material may include a thermoformed multilayer sheet. The first aligner material may be a lithography-based photo polymerized resin.

In some embodiments, the method may also include identifying in the treatment plan a prescribed time for the first aligner, identifying, based on the first determination, an effective time of the first aligner, the effective time associated with the specified reduction in force, and determining, based on a comparison of the effective time and the prescribed time, whether or not to use the prescribed time for the first aligner.

The method may also include providing a recommendation to accelerate implementation of a second aligner used to move the one or more teeth in accordance with a second stage of the treatment plan if the effective time of the first aligner is less than the prescribed time.

In some embodiments, the method may include providing a recommendation to decelerate implementation of a second aligner used to move the one or more teeth in accordance with a second stage of the treatment plan if the effective time of the first aligner is greater than the prescribed time.

The region may correspond to a leading tooth of the one or more teeth. The region may be distributed about the first aligner.

A method for fabricating an aligner is disclosed. The method may include accessing a treatment plan for treating a dentition of a patient, identifying a first aligner to implement a first stage of the treatment plan, identifying a physical quality of a region of the first aligner correlated with force applied by the first aligner during the first stage of the treatment plan, identifying a threshold value of the physical quality, the threshold value corresponding to a reduction in the force to the teeth applied by the first aligner during the first stage of the treatment plan, identifying a sensor configured to sense whether a value of the physical quality can fall below the threshold value, and coupling the sensor to the region of the first aligner.

In some embodiments, the physical quality corresponds to a material stress or a material strain of a material of the first aligner. In some embodiments, the sensor includes an embedded stress sensor embedded into the region of the first aligner, the embedded stress sensor being configured to sense a movement of the region of the first aligner and to provide a change in electrical conductivity based on the sensed movement.

In some embodiments, sensor includes one or more microfluidic channels configured to sense a capacitance of the region of the first aligner and to identify a spatially distributed strain on the region of the first aligner based on the sensed capacitance.

In some embodiments, the sensor includes a plurality of legs configured to sense a distance therebetween and to identify a spatially distributed strain on the region of the first aligner based on the sensed distance.

The threshold value may be associated with a relaxation of a first aligner material of the first aligner beyond a relaxation threshold. The first aligner material may include a thermoformed multilayer sheet. The first aligner material may include a lithography-based photo polymerized resin. In some embodiments, the region corresponds to a leading tooth of the one or more teeth. The first stage of the treatment plan may be configured to move the leading tooth more than other teeth of the one or more teeth.

A method for quantifying a corrective force applied to a patient's teeth by a dental repositioning appliance is disclosed. The method may include providing a dental repositioning appliance comprising one or more sensors positioned adjacent to one or more teeth when the dental repositioning appliance is worn by the patient, transmitting one or more signals generated by the one or more sensors to an external signal processor, and calculating a corrective force vector from the one or more signals and the positions of the one or more sensors.

In some embodiments, the method may also include calculating a rate of movement for the one or more teeth based on the one or more signals and the positions of the one or more sensors.

In some embodiments, the dental repositioning appliance may include a plurality of tooth-cavities configured to receive the patient's teeth and exert repositioning forces thereon.

The one or more sensors are selected from the group consisting of piezoelectric strain sensors, nanoparticle-based strain sensors, optical strain sensors, and capacitive sensing array sensors.

In some embodiments, the one or more signals generated by the one or more sensors comprise stress data, strain data, displacement data, or any combination thereof.

In some embodiments, the transmitting step may include wireless transmission of the one or more signals. The wireless transmission includes use of wifi or bluetooth data transmission. In some embodiments, the external signal processor comprises a cell phone, a laptop computer, a personal computer, or a computer system.

In some embodiments, data for the one or more signals is stored locally on a cell phone, a laptop computer, a personal computer, or a computer system. In some embodiments, data for the one or more signals is stored in a cloud-based database.

In some embodiments, the transmitting step may be performed continuously or the transmitting step may be performed discontinuously.

In some embodiments, the transmitting step may be performed periodically or transmitting step may be performed at random intervals of time.

In some embodiments, a calculated value of the corrective force vector is used to determine when the dental repositioning appliance should be removed or replaced. In some embodiments, a calculated rate of movement for the one or more teeth is used to adjust a treatment schedule for a patient.

A dental repositioning appliance is disclosed. The appliance may include a removable polymeric shell appliance that conforms to the shape of the patient's teeth but is slightly out of alignment with an initial or immediately prior tooth configuration, and one or more sensors positioned adjacent to one or more teeth when the dental repositioning appliance is worn by a patient.

In some embodiments, the one or more sensors are configured for wireless transmission of one or more signals generated by the one or more sensors to an external signal processing device. In some embodiments, the one or more sensors are selected from the group consisting of piezoelectric strain sensors, nanoparticle-based strain sensors, optical strain sensors, and capacitive sensing array sensors.

The one or more signals generated by the one or more sensors may include stress data, strain data, displacement data, or any combination thereof.

In some embodiments, the external signal processing device is configured to calculate a corrective force vector from the one or more signals and the positions of the one or more sensors. The external signal processing device may be configured to calculate a rate of movement for the one or more teeth based on the one or more signals and the positions of the one or more sensors.

A system is disclosed. The system may include one or more dental repositioning appliances including: a removable polymeric shell appliance that conforms to the shape of a patient's teeth but is slightly out of alignment with an initial or immediately prior tooth configuration, and one or more sensors positioned adjacent to one or more teeth when the dental repositioning appliance is worn by the patient, an external signal processing device, wherein the one or more sensors are configured for wireless transmission of one or more signals generated by the one or more sensors to the external signal processing device and the external signal processing device is configured to calculate a corrective force vector or a rate of movement for the one or more teeth.

In some embodiments, the one or more sensors are selected from the group consisting of piezoelectric strain sensors, nanoparticle-based strain sensors, optical strain sensors, and capacitive sensing array sensors. The one or more signals generated by the one or more sensors may include stress data, strain data, displacement data, or any combination thereof.

The external signal processor may include a cell phone, a laptop computer, a personal computer, or a computer system. Data for the one or more signals may be stored locally on a cell phone, a laptop computer, a personal computer, or a computer system. The data for the one or more signals may be stored in a cloud-based database.

A method for designing a dental repositioning appliance is disclosed. The method may include creating a model of a patient's set of teeth, specifying a desired final position for one or more teeth in the patient's set of teeth, creating a treatment plan comprising a sequence of steps for repositioning one or more teeth so that they conform to the desired final position(s), and fabricating the dental repositioning appliance, wherein a sensor is placed on each of the one or more teeth to be repositioned and on an adjacent tooth for each of the one or more teeth to be repositioned. The model may be a physical model. The model may be a 3D digital model.

In some embodiments, the step of creating a treatment plan includes identifying one or more teeth that exhibit a highest rate of movement.

In some embodiments, the step of creating a treatment plan may include identifying one or more teeth that will require the highest level of force or torque to reposition.

In some embodiments, the one or more sensors comprise adhesive-backed sensors that are adhered to a surface of a thermoformed dental repositioning appliance. In some embodiments, the one or more sensors are inserted into a designed feature in a 3D printed dental repositioning appliance. In some embodiments, the one or more sensors are selected from the group consisting of piezoelectric strain sensors, nanoparticle-based strain sensors, optical strain sensors, and capacitive sensing array sensors.

In some embodiments, the method also includes modifying a treatment plan based strain data from the sensor.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A: isometric view. FIG. 4B: top view. FIG. 4C: a slice view comprising a stress and/or strain sensor on an exterior surface of an appliance. FIG. 4D: a slice view comprising a stress and/or strain sensor on an interior surface of an appliance. FIG. 4E: a slice view comprising a stress and/or strain sensor interior to the body of an appliance.

FIG. 5A: top view. FIG. 5B: isometric view. FIG. 5C: transparent view comprising channels interior to the body of an appliance. FIG. 5D: slice view comprising channels on an interior surface. FIG. 5E: slice view comprising channels on an exterior surface.

DETAILED DESCRIPTION

Figure 1A:
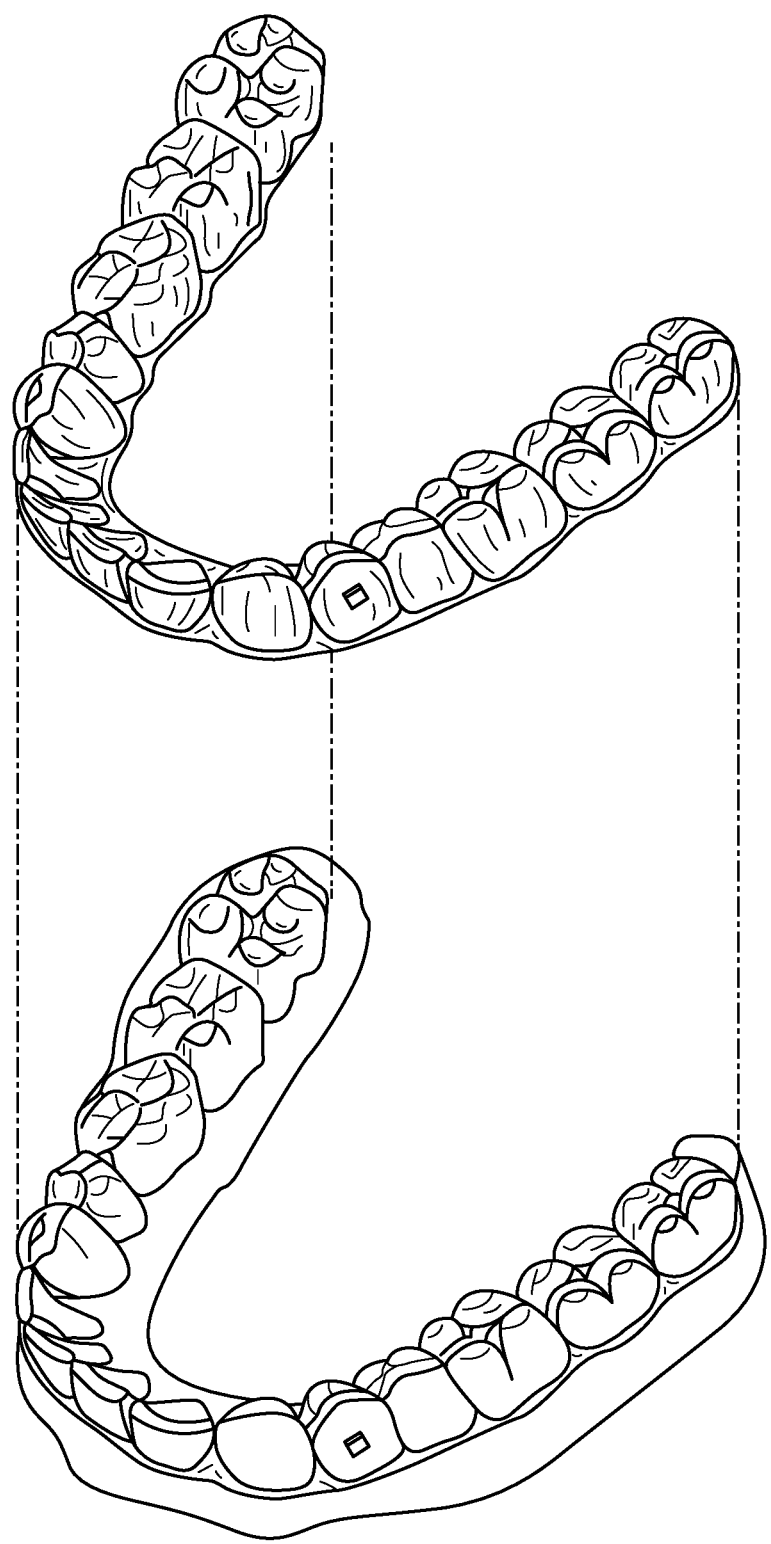
FIG. 1A illustrates a tooth repositioning appliance, in accordance with one or more aspects of the devices disclosed herein.

A better understanding of the features and advantages of the disclosed methods, devices, and systems will be obtained by reference to the following detailed description and the accompanying drawings. Although the detailed description contains many specifics, these should not be construed as limiting the scope of the disclosure. Rather, they should be construed as merely illustrating specific examples and different aspects of the present disclosure. It should be appreciated that the scope of the disclosure includes other embodiments not discussed in detail. Various other modifications, changes, and variations which will be apparent to those skilled in the art may be made in the arrangement, operation, and details of the methods, devices, and systems provided herein without departing from the spirit and scope of the disclosure.

The present disclosure provides methods, devices, and/or systems for making treatment plans more effective. The appliances used for many treatment plans are designed/manufactured with physical qualities (e.g., rigidity) in mind that allow the appliances to exert repositioning forces on teeth. Intentional mismatches between cavity geometries of appliances and the teeth that they receive often cause application of forces to move the teeth. Conventional treatment plans prescribe a set amount of time for each stage, as the actual performance of an aligner in a patient's mouth is often not known at the time of design/manufacture (but rather is typically estimated based on, e.g., past cases or the properties of the material used to form the aligner). Examples of the time for such stages include a week, two weeks, three week, four weeks, etc. In the real world, however, individual rates of tooth movement vary on a variety of factors, such as a patient's age/gender/health/race/etc., particularities of the patient's body, the complexity of a patient's treatment, and the patient's overall responsiveness to treatment. As a result, in many cases, a treatment plan may prescribe aligners for a stage for days or even weeks even though the material properties of these aligners have relaxed (e.g., are no longer providing intended forces) or the teeth have moved near their intended position for that stage. Depending on various factors, such as the treatment stage, the age/gender/health/etc. of the patient, and the type of treatment, many types of aligner material lose their rigidity at different times. As a result, many treatment plans prescribe aligners after the efficacy of those aligners, or even worse, prescribe changing aligners before a patient's teeth have advanced to a subsequent stage.

According to the techniques herein, one or more sensors coupled to an aligner (embedded into the aligner, incorporated as fluidic channels, etc.) are used to sense one or more physical qualities of the aligner to determine whether the physical qualities indicate that the aligner material has relaxed and has, e.g., reduced the force systems applied to teeth and/or that the teeth movement for the stage has slowed down. The sensors may provide a signal that represents whether or not the physical qualities (stress, strain, etc.) fall below a threshold value. A treatment plan may be modified if needed. These techniques have the potential to make treatment plans faster and more effective by speeding up some stages while making sure some (perhaps other) stages are implemented only after the teeth are near the appropriate position.

The present disclosure provides methods, devices, and systems for monitoring the efficacy of a dental appliance, e.g., a dental repositioning appliance or "aligner", in terms of the repositioning forced applied to a patient's teeth, and for indicating when the dental appliance should be removed or replaced. The disclosed methods and devices allow one to collect data on and account for individual variance of tooth movement rates, thus allowing for optimization of a treatment plan for individual patients (e.g., by adjusting the time required for each of a series of aligners to be worn by the patient) and leading to improved outcomes in the final tooth alignment achieved. Currently, determination of a treatment schedule may be typically based on the judgement of a physician, but judgement may vary between physicians and lead to inconsistency in the results achieved for different patients. Alternatively, determination of a treatment schedule may be related to a standardized time between aligner changes; however, if a patient's teeth move faster, the time between aligners may be shortened resulting in less total treatment time.

The disclosed devices, e.g., customized aligner change indicator devices, consist of dental repositioning appliances or aligners that may comprise embedded stress/strain sensors (or sensors based on other material properties or mechanisms) to monitor the strength of a "correction" force applied to the patient's teeth and/or to indicate when the aligner no longer provides a sufficient "correction" force to the teeth to affect further change in tooth position. As noted above, in some aspects, the disclosed dental repositioning appliances or aligners also enable collection of data on tooth movement rates in individual patients. Instead of applying a universal schedule of one or two weeks of wear for each dental repositioning appliance in a series, the embedded sensor devices and/or systems of the present disclosure may be used to provide an exact and customized schedule for changing to the next dental repositioning appliance for patients with slower or faster teeth movement rates.

There are several different approaches or mechanisms that may be used to detect when the aligner no longer provides an adequate "correction" force including, but not limited to, use of embedded stress/strain sensors, use of polarized light, use of capacitive sensing arrays, or any combination thereof, as will be discussed in more detail below.

In some aspects, the systems disclosed herein may comprise an application, such as a cell phone application, that synchronizes with the stress/strain data and/or other appropriate sensor signals and provides user access to the data. The application may record the stress/strain data and/or other signal data, which may then be used not only to inform patients when it is time to change the aligner, but also may be used to collect valuable information on tooth movement rates from patients.

In some aspects, the systems of the present disclosure may comprise the dental appliance, a means for measuring the efficacy of the dental appliance, a data network which may include a means of data transmission, a means for data storage, a means for data analysis, a means of accessing and/or viewing the data provided by the dental appliance, a cell phone application to facilitate the latter, or any combination thereof.

Example Terms

Unless otherwise defined, all technical terms used herein have the same meaning as commonly understood by one of ordinary skill in the art in the field to which this disclosure belongs.

As used in this specification and the appended claims, the singular forms "a", "an", and "the" include plural references unless the context clearly dictates otherwise.

As used herein the term "and/or" may be used as a functional word to indicate that two words or expressions are to be taken together or individually. For example, the phrase "A and/or B" encompasses A alone, B alone, and A and B together. Depending on context, the term "or" need not exclude one of a plurality of words/expressions. As an example, the phrase "A or B" need not exclude A and B together.

As used herein the terms "dental appliance," and "tooth receiving appliance" are treated synonymously. As used herein, a "dental positioning appliance", an "orthodontic appliance", or an "aligner" may be treated synonymously, and may include any dental appliance configured to change the position of a patient's teeth in accordance with a plan, such as an orthodontic treatment plan. A "dental positioning appliance", "orthodontic appliance", or "aligner" as used herein, may include a set of dental appliances configured to incrementally change the position of a patient's teeth over time. As noted herein, dental positioning appliances, orthodontic appliances, and/or aligners may comprise polymeric appliances configured to move a patient's teeth in accordance with an orthodontic treatment plan. The polymeric appliances may have an interior surface that forms tooth-receiving cavities. As noted herein, due to interactions between these tooth-receiving cavities and a patient's dentition, dental positioning appliances may exert repositioning forces on the patient's dentition, sometimes in stages, to implement an orthodontic treatment plan.

As used herein the terms "torque" and "moment" are treated synonymously.

A "physical qualities" may include any property of a material that can be measured without changing the composition of the material. Examples of physical qualities include stress (aka material stress), strain (aka material strain), force(s) applied, displacement, etc. "Relaxation" of an aligner, as used herein, may include a physical quality of the aligner that signifies the aligner is no longer applying a significant part of its intended force systems. Relaxation of an aligner may be associated with a patient's teeth nearing a stage of a subsequent aligner of a treatment plan. Relaxation of an aligner may be identified by material strains on portions of the aligner (as noted herein), by the aligner approximating the shape of a subsequent aligner in the treatment plan, by a patient's dentition being able to receive a subsequent aligner, etc.

As used herein a "moment" may encompass a force acting on an object such as a tooth at a distance from a center of resistance. The moment may be calculated with a vector cross product of a vector force applied to a location corresponding to a displacement vector from the center of resistance, for example. The moment may comprise a vector pointing in a direction. A moment opposing another moment may encompass one of the moment vectors oriented toward a first side of the object such as the tooth and the other moment vector oriented toward an opposite side of the object such as tooth, for example. Any discussion herein referring to application of forces on a patient's teeth is equally applicable to application of moments on the teeth, and vice-versa.

As used herein a "plurality of teeth" may encompass two or more teeth. A "leading tooth," as used herein, may include a tooth that experiences a greater degree of motion than other teeth in an arch at a stage of at treatment plan. For instance, a stage of a treatment plan may cause a leading tooth to move more than the teeth surrounding it. A plurality of teeth may, but need not, comprise adjacent teeth. In some embodiments, one or more posterior teeth comprises one or more of a molar, a premolar or a canine, and one or more anterior teeth comprising one or more of a central incisor, a lateral incisor, a cuspid, a first bicuspid or a second bicuspid.

Dental Appliances

The present disclosure provides orthodontic appliances and related methods, devices, and systems. Repositioning of teeth may be accomplished with the use of a series of removable dental appliances such as the Invisalign® system available from Align Technology, Inc., the assignee of the present disclosure. Such appliances may be a thin shell of polymeric material having tooth receiving cavities shaped to receive a patient's teeth and apply controlled forces to the teeth to gradually move the teeth into the new configuration. Repetition of this process with successive appliances comprising new configurations eventually moves the teeth through a series of intermediate configurations or alignment patterns to a final desired configuration. Repositioning of teeth may be accomplished through other series of removable orthodontic and/or dental appliances, including polymeric shell appliances.

Although reference is made to an appliance comprising a polymeric shell, the methods disclosed herein are well suited for use with many appliances that receive teeth, for example appliances without one or more polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication as described herein, for example. Alternatively or in combination, the appliance can be fabricated using a machining process, such as in the case of an appliance fabricated from a block of material using computer numeric control (CNC) machining. Additionally, although reference is made herein to orthodontic appliances, at least some of the techniques described herein may apply to restorative and/or other dental appliances, including without limitation crowns, veneers, teeth-whitening appliances, teeth-protective appliances, etc.

In some aspects, the dental appliances disclosed herein may be well suited for combination with one or more commercially-available tooth moving components, such as attachments and polymeric shell appliances. In some aspects, the dental appliance and one or more attachments are configured to move one or more teeth along a tooth movement vector comprising six degrees of freedom, in which three degrees of freedom are rotational and three degrees of freedom are translation.

In some aspects, the dental appliances disclosed herein may be well suited for moving one or more teeth along a specified tooth movement vector. For example, in some aspects, the disclosed dental appliances may be well suited for repositioning of one tooth, two teeth, three teeth, four teeth, five teeth, six teeth, seven teeth, eight teeth, nine teeth, ten teeth, or more. In some aspects, the disclosed dental appliances may be suited for repositioning all or a portion of the full human complement of 32 teeth.

In some aspects, the dental appliances disclosed herein may be well suited for moving one or more teeth of a first group of one or more teeth, or moving one or more teeth of a second group of one or more teeth, or moving one or more teeth of a third group of teeth, or a combination thereof.

In some aspects, the dental appliances disclosed herein may be well suited for tracking the rate of movement (or velocity) of one or more teeth along a specified tooth movement vector, e.g., by tracking the rate at which the local strain changes and calibrating said changes in terms of a displacement distance per unit time. For example, in some aspects, the disclosed dental appliances may be well suited for tracking the rate of movement (or velocity) of one tooth, two teeth, three teeth, four teeth, five teeth, six teeth, seven teeth, eight teeth, nine teeth, ten teeth, or more. In some aspects, the disclosed dental appliances may be suited for tracking the rate of movement (or velocity) of all or a portion of the full human complement of 32 teeth. The appliances may track rates of movement of or between any two of 0.005 mm/stage, 0.05 mm/stage, 0.10 mm/stage, 0.15 mm/stage, 0.20 mm/stage, 0.25 mm/stage, 0.30 mm/stage, 0.35 mm/stage, 0.40 mm/stage, 0.45 mm/stage, 0.50 mm/stage, 0.60 mm/stage, 0.70 mm/stage, 0.80 mm/stage, 0.90 mm/stage, 1.0 mm/stage, or faster.

Dental Appliance Fabrication

The various embodiments of the orthodontic appliances (e.g., dental repositioning appliances) presented herein can be fabricated in a wide variety of ways. In some embodiments, the orthodontic appliances herein (or portions thereof) can be produced using direct fabrication, such as additive manufacturing techniques (also referred to herein as "3D printing") or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

In some embodiments, the direct fabrication methods provided herein build up the object geometry in a layer-by-layer fashion, with successive layers being formed in discrete build steps. Alternatively or in combination, direct fabrication methods that allow for continuous build-up of an object's geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, (corresponding to U.S. Pat. Nos. corresponding to U.S. Pat. Nos. 9,205,601, 9,216, 546, and 9,211,678) the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous 3D path in order to form the object. Such methods are described in U.S. Patent Publication No. 2014/0061974, corresponding to U.S. Pat. No. 9,511,543, the disclosures of which are incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, corresponding to U.S. Pat. No. 9,321,215, the disclosures of which are incorporated herein by reference in its entirety.

The direct fabrication approaches provided herein are compatible with a wide variety of materials, including but not limited to one or more of the following: polymer matrix reinforced with ceramic or metallic polymers, a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step using the same fabrication machine and method. For instance, a multi-tip extrusion apparatus can be used to selectively dispense multiple types of materials (e.g., resins, liquids, solids, or combinations thereof) from distinct material supply sources in order to fabricate an object from a plurality of different materials. Such methods are described in U.S. Pat. No. 6,749,614, the disclosure of which is incorporated herein by reference in its entirety. Alternatively or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed. The relative arrangement of the first and second portions can be varied as desired, e.g., the first portion can be partially or wholly encapsulated by the second portion of the object. The sequential manufacturing steps can be performed using the same fabrication machine or different fabrication machines, and can be performed using the same fabrication method or different fabrication methods. For example, a sequential multi-manufacturing procedure can involve forming a first portion of the object using stereolithography and a second portion of the object using fused deposition modeling.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the 3D geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that may be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

In some embodiments, the direct fabrication methods described herein implement process controls for various machine parameters of a direct fabrication system or device in order to ensure that the resultant appliances are fabricated with a high degree of precision. The precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical qualities (e.g., modulus, strength, elongation) and/or thermal properties (e.g., glass transition temperature, heat deflection temperature). Process control for a material manufacturing process can be achieved with screening of raw materials for physical qualities and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every nth build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

Although various embodiments herein are described with respect to direct fabrication techniques, it shall be appreciated that other techniques can also be used, such as indirect fabrication techniques. In some embodiments, the appliances herein (or portions thereof) can be produced using indirect fabrication techniques, such as by thermoforming over a positive or negative mold. Indirect fabrication of an orthodontic appliance can involve one or more of the following steps: producing a positive or negative mold of the patient's dentition in a target arrangement (e.g., by additive manufacturing, milling, etc.), thermoforming one or more sheets of material over the mold in order to generate an appliance shell, forming one or more structures in the shell (e.g., by cutting, etching, etc.), and/or coupling one or more components to the shell (e.g., by extrusion, additive manufacturing, spraying, thermoforming, adhesives, bonding, fasteners, etc.). Optionally, one or more auxiliary appliance components as described herein (e.g., elastics, wires, springs, bars, arch expanders, palatal expanders, twin blocks, occlusal blocks, bite ramps, mandibular advancement splints, bite plates, pontics, hooks, brackets, headgear tubes, bumper tubes, palatal bars, frameworks, pin-and-tube apparatuses, buccal shields, buccinator bows, wire shields, lingual flanges and pads, lip pads or bumpers, protrusions, divots, etc.) are formed separately from and coupled to the appliance shell (e.g., via adhesives, bonding, fasteners, mounting features, etc.) after the shell has been fabricated.

In some embodiments, the orthodontic appliances herein can be fabricated using a combination of direct and indirect fabrication techniques, such that different portions of an appliance can be fabricated using different fabrication techniques and assembled in order to form the final appliance. For example, an appliance shell can be formed by indirect fabrication (e.g., thermoforming), and one or more structures or components as described herein (e.g., auxiliary components, power arms, etc.) can be added to the shell by direct fabrication (e.g., printing onto the shell).

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled additive manufacturing such as 3D printing, etc.). The computer-based methods presented herein can improve the accuracy, flexibility, and convenience of appliance fabrication.

In some embodiments, computer-based 3D planning/design tools, such as Treat™ software from Align Technology, Inc., may be used to design and fabricate the orthodontic appliances described herein.

Tooth Repositioning Appliances and Systems

Turning now to the drawings, in which like numbers designate like elements in the various figures, FIG. 1A illustrates an exemplary tooth repositioning appliance or aligner 100 that can be worn by a patient in order to achieve an incremental repositioning of individual teeth 102 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. The physical model (e.g., physical mold) of teeth can be formed through a variety of techniques, including 3D printing. The appliance can be formed by thermoforming the appliance over the physical model. In some embodiments, a physical appliance is directly fabricated, e.g., using additive manufacturing techniques, from a digital model of an appliance. In some embodiments, the physical appliance may be created through a variety of direct formation techniques, such as 3D printing. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some, most, or even all of the teeth will be repositioned at some point during treatment. Teeth that are moved can also serve as a base or anchor for holding the appliance as it is worn by the patient.

In some embodiments, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the URL "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450. Examples of materials used to fabricate appliances include the materials described in U.S. Pat. No. 9,655,693, entitled "Multilayer dental appliances and related methods and systems;" U.S. Prov. App. Ser. No. 62/677,354, entitled "CURABLE COMPOSITION FOR USE IN A HIGH TEMPERATURE LITHOGRAPHY-BASED PHOTOPOLYMERIZATION PROCESS AND METHOD OF PRODUCING CROSS-LINKED POLYMERS THEREFROM;" and U.S. Prov. App. Ser. No. 62/677,364 entitled "POLYMERIZABLE MONOMERS AND METHOD OF POLYMERIZING THE SAME;" the contents of all of these foregoing applications being incorporated by reference as if set forth fully herein.

Optionally, in cases involving more complex movements or treatment plans, it may be beneficial to utilize auxiliary components (e.g., features, accessories, structures, devices, components, and the like) in conjunction with an orthodontic appliance. Examples of accessories include but are not limited to elastics, wires, springs, bars, arch expanders, palatal expanders, twin blocks, occlusal blocks, bite ramps, mandibular advancement splints, bite plates, pontics, hooks, brackets, headgear tubes, springs, bumper tubes, palatal bars, frameworks, pin-and-tube apparatuses, buccal shields, buccinator bows, wire shields, lingual flanges and pads, lip pads or bumpers, protrusions, divots, and the like. In some embodiments, the appliances, systems and methods described herein include improved orthodontic appliances with integrally formed features that are shaped to couple to auxiliary components, or that replace auxiliary components.

Figure 1B:
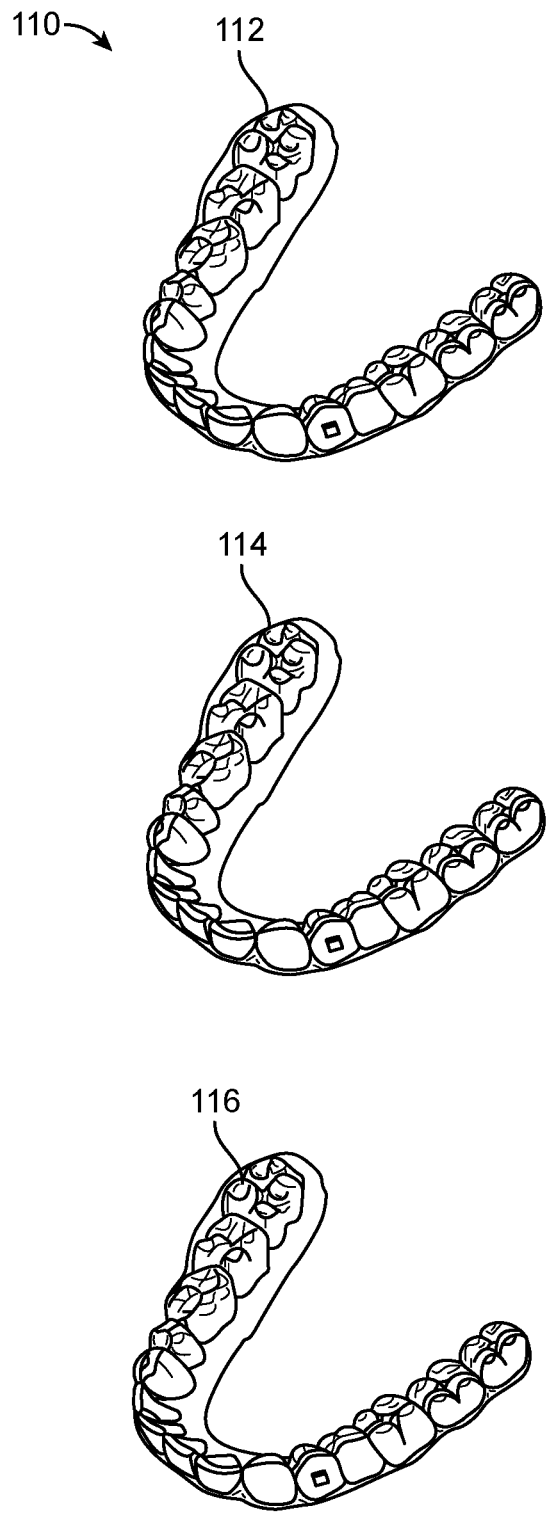
FIG. 1B illustrates a tooth repositioning system, in accordance with one or more aspects of the systems disclosed herein.

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement towards a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 1C:
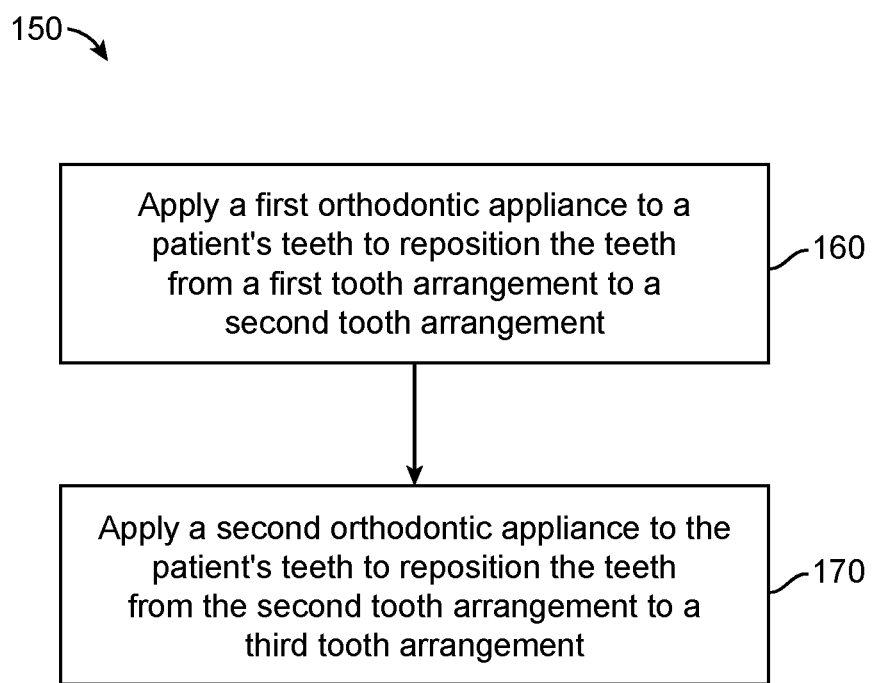
FIG. 1C illustrates a method of orthodontic treatment using a plurality of appliances, in accordance with one or more aspects of the methods disclosed herein.

FIG. 1C illustrates a method 150 of orthodontic treatment using a plurality of appliances, in accordance with embodiments. The method 150 can be practiced using any of the appliances or appliance sets described herein. In block 160, a first orthodontic appliance is applied to a patient's teeth in order to reposition the teeth from a first tooth arrangement to a second tooth arrangement. In block 170, a second orthodontic appliance is applied to the patient's teeth in order to reposition the teeth from the second tooth arrangement to a third tooth arrangement. The method 150 can be repeated as necessary using any suitable number and combination of sequential appliances in order to incrementally reposition the patient's teeth from an initial arrangement to a target arrangement. The appliances can be generated all at the same stage or in sets or batches (at the beginning of a stage of the treatment, at an intermediate stage of treatment, etc.), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that may (if fully achieved) move individual teeth beyond the tooth arrangement that has been selected as the "final." Over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Figure 2:
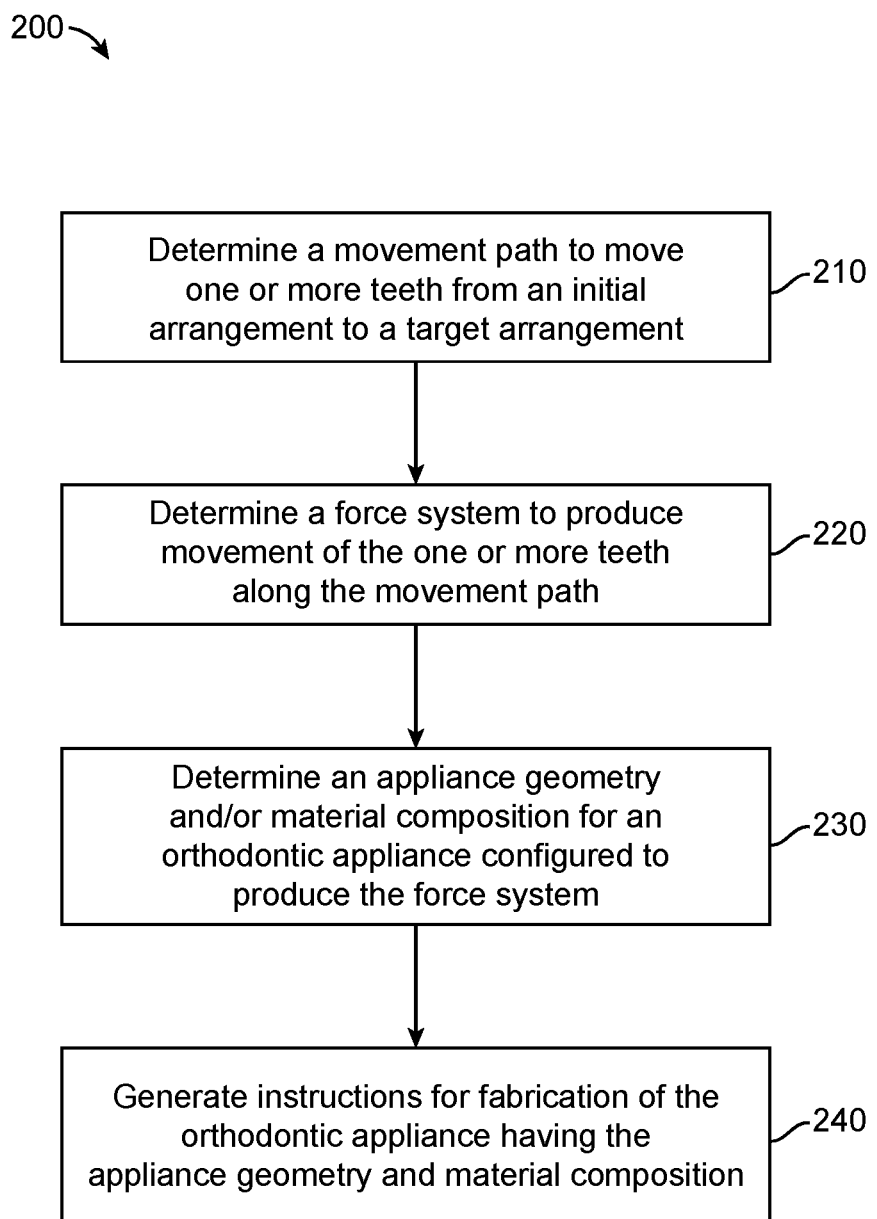
FIG. 2 illustrates a method for designing an orthodontic appliance, in accordance with one or more aspects of the methods disclosed herein.

FIG. 2 illustrates a method 200 for designing an orthodontic appliance to be fabricated, in accordance with embodiments. The method 200 can be applied to any embodiment of the orthodontic appliances described herein. Some or all of the operations of the method 200 can be performed by any suitable data processing system or device, e.g., one or more processors configured with suitable instructions.

In block 210, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In block 220, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

Determination of the force system can be performed in a variety of ways. For example, in some embodiments, the force system is determined on a patient-by-patient basis, e.g., using patient-specific data. Alternatively or in combination, the force system can be determined based on a generalized model of tooth movement (e.g., based on experimentation, modeling, clinical data, etc.), such that patient-specific data is not necessarily used. In some embodiments, determination of a force system involves calculating specific force values to be applied to one or more teeth to produce a particular movement. Alternatively, determination of a force system can be performed at a high level without calculating specific force values for the teeth. For instance, block 220 can involve determining a particular type of force to be applied (e.g., extrusive force, intrusive force, translational force, rotational force, tipping force, torqueing force, etc.) without calculating the specific magnitude and/or direction of the force.

In block 230, an appliance geometry and/or material composition for an orthodontic appliance configured to produce the force system is determined. The appliance can be any embodiment of the appliances discussed herein, such as an appliance having variable localized properties, integrally formed components, and/or power arms.

For example, in some embodiments, the appliance comprises a heterogeneous thickness, a heterogeneous stiffness, or a heterogeneous material composition. In some embodiments, the appliance comprises two or more of a heterogeneous thickness, a heterogeneous stiffness, or a heterogeneous material composition. In some embodiments, the appliance comprises a heterogeneous thickness, a heterogeneous stiffness, and a heterogeneous material composition. The heterogeneous thickness, stiffness, and/or material composition can be configured to produce the force system for moving the teeth, e.g., by preferentially applying forces at certain locations on the teeth. For example, an appliance with heterogeneous thickness can include thicker portions that apply more force on the teeth than thinner portions. As another example, an appliance with heterogeneous stiffness can include stiffer portions that apply more force on the teeth than more elastic portions. Variations in stiffness can be achieved by varying the appliance thickness, material composition, and/or degree of photopolymerization, as described herein.

In some embodiments, determining the appliance geometry and/or material composition comprises determining the geometry and/or material composition of one or more integrally formed components to be directly fabricated with an appliance shell. The integrally formed component can be any of the embodiments described herein. The geometry and/or material composition of the integrally formed component(s) can be selected to facilitate application of the force system onto the patient's teeth. The material composition of the integrally formed component can be the same as or different from the material composition of the shell.

In some embodiments, determining the appliance geometry comprises determining the geometry for a variable gable bend.

The block 230 can involve analyzing the desired force system in order to determine an appliance geometry and material composition that may produce the force system. In some embodiments, the analysis involves determining appliance properties (e.g., stiffness) at one or more locations that may produce a desired force at the one or more locations. The analysis can then involve determining an appliance geometry and material composition at the one or more locations to achieve the specified properties. Determination of the appliance geometry and material composition can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including finite element analysis packages from ANSYS, Inc., of Canonsburg, Pa., and SIMULIA (Abaqus) software products from Dassault Systèmes of Waltham, Mass.

Optionally, one or more appliance geometries and material compositions can be selected for testing or force modeling. As noted above, a desired tooth movement, as well as a force system required or desired for eliciting the desired tooth movement, can be identified. Using the simulation environment, a candidate appliance geometry and composition can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

Optionally, block 230 can further involve determining the geometry of one or more auxiliary components to be used in combination with the orthodontic appliance in order to exert the force system on the one or more teeth. Such auxiliaries can include one or more of tooth-mounted attachments, elastics, wires, springs, bite blocks, arch expanders, wire-and-bracket appliances, shell appliances, headgear, or any other orthodontic device or system that can be used in conjunction with the orthodontic appliances herein. The use of such auxiliary components may be advantageous in situations where it is difficult for the appliance alone to produce the force system. Additionally, auxiliary components can be added to the orthodontic appliance in order to provide other desired functionalities besides producing the force system, such as mandibular advancement splints to treat sleep apnea, pontics to improve aesthetic appearance, and so on. In some embodiments, the auxiliary components are fabricated and provided separately from the orthodontic appliance. Alternatively, the geometry of the orthodontic appliance can be modified to include one or more auxiliary components as integrally formed components.

In block 240, instructions for fabrication of the orthodontic appliance having the appliance geometry and material composition are generated. The instructions can be configured to control a fabrication system or device in order to produce the orthodontic appliance with the specified appliance geometry and material composition. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.). Optionally, the instructions can be configured to cause a fabrication machine to directly fabricate the orthodontic appliance with teeth receiving cavities having variable gable bends, as discussed above and herein. In alternative embodiments, the instructions can be configured for indirect fabrication of the appliance, e.g., by thermoforming.

Although the above blocks show a method 200 of designing an orthodontic appliance in accordance with some embodiments, a person of ordinary skill in the art will recognize some variations based on the teaching described herein. Some of the blocks may comprise sub-blocks. Some of the blocks may be repeated as often as desired. One or more blocks of the method 200 may be performed with any suitable fabrication system or device, such as the embodiments described herein. Some of the blocks may be optional, and the order of the blocks can be varied as desired. For instance, in some embodiments, block 220 is optional, such that block 230 involves determining the appliance geometry and/or material composition based directly on the tooth movement path rather than based on the force system.

Figure 3:
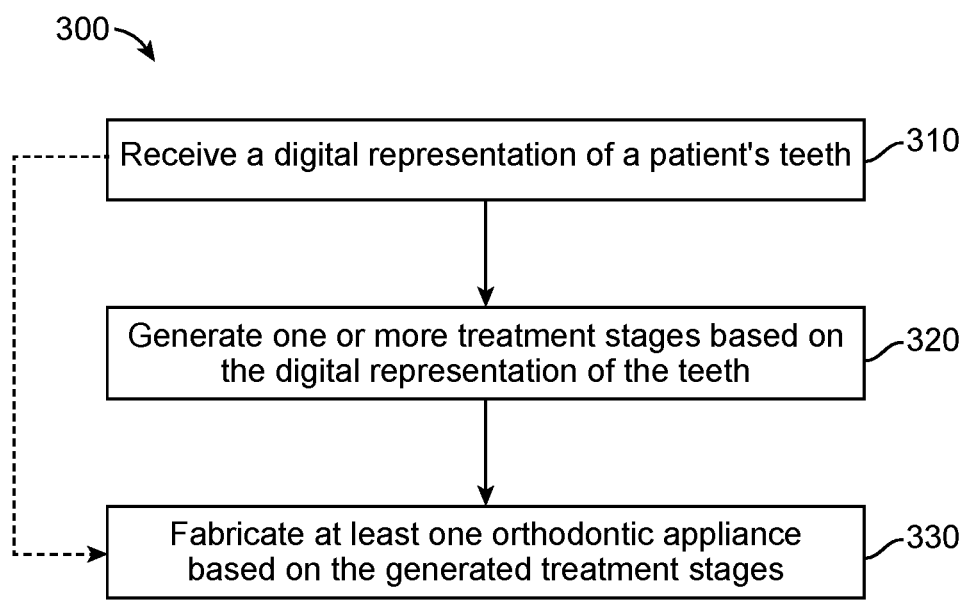
FIG. 3 illustrates a method for planning an orthodontic treatment, in accordance with one or more aspects of the methods disclosed herein.

FIG. 3 illustrates a method 300 for digitally planning an orthodontic treatment and/or design or fabrication of an appliance, in accordance with embodiments. The method 300 can be applied to any of the treatment procedures described herein and can be performed by any suitable data processing system.

In block 310, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In block 320, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In block 330, at least one orthodontic appliance is fabricated based on the generated treatment stages. For example, a set of appliances can be fabricated, each shaped according to a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 3, design and/or fabrication of an orthodontic appliance, and perhaps a particular orthodontic treatment, may include use of a representation of the patient's teeth (e.g., receive a digital representation of the patient's teeth 310), followed by design and/or fabrication of an orthodontic appliance based on a representation of the patient's teeth in the arrangement represented by the received representation.

Optionally, some or all of the blocks of the method 300 are performed locally at the site where the patient is being treated and during a single patient visit, referred to herein as "chair side manufacturing." Chair side manufacturing can involve, for example, scanning the patient's teeth, automatically generating a treatment plan with treatment stages, and immediately fabricating one or more orthodontic appliance(s) to treat the patient using a chair side direct fabrication machine, all at the treating professional's office during a single appointment. In embodiments where a series of appliances are used to treat the patient, the first appliance may be produced chair side for immediate delivery to the patient, with the remaining appliances produced separately (e.g., off site at a lab or central manufacturing facility) and delivered at a later time (e.g., at a follow up appointment, mailed to the patient). Alternatively, the methods herein can accommodate production and immediate delivery of the entire series of appliances on site during a single visit. Chair side manufacturing can thus improve the convenience and speed of the treatment procedure by allowing the patient to immediately begin treatment at the practitioner's office, rather than having to wait for fabrication and delivery of the appliances at a later date. Additionally, chair side manufacturing can provide improved flexibility and efficiency of orthodontic treatment. For instance, in some embodiments, the patient is re-scanned at each appointment to determine the actual positions of the teeth, and the treatment plan is updated accordingly. Subsequently, new appliances can be immediately produced and delivered chair side to accommodate any changes to or deviations from the treatment plan.

Dental Repositioning Appliances Comprising Sensors

When using a dental appliance, such as an aligner, in orthodontic treatment, a patient may wear the appliance until the patient's teeth have moved or repositioned to the tooth configuration prescribed by the appliance. When the teeth substantially reach the desired configuration, the force may approach zero. Alternatively, a dental appliance may wear out over time due to humidity and heat in the mouth. In the case of aligner fatigue, the aligner may no longer apply adequate force when worn due fatigue. In either case, the useful life of such an appliance for applying a repositioning force has ended. Subsequently, the patient may progress to the next appliance for repositioning to the next tooth configuration (e.g. stage) in the treatment plan. The new appliance may apply repositioning forces to move the teeth to the next desired configuration, repeating the appliance wear cycle. An indication that the appliance may not be supplying significant repositioning forces may be beneficial in the determination of when and if to advance the patient to the next appliance or next stage of treatment. The Aligner may also be defective and/or have been exposed to environmental conditions and/or been mishandled such that it no longer has provides the desired repositioning forces, such as by providing too little or too much force. In some embodiments, the sensors can aid in determining whether the aligner has changed since manufacturing, such that the system can alert the patient or prescribing person, such as a dental professional, that the aligner may be defective or need to be placed—in such a manner the sensors can keep the progress of the treatment on track.

Due to individual variance in tooth movement rates and/or the amount of time and force required to achieve intermediate and final tooth patterns, the schedule for changing dental appliances, such as aligners, may be customized for each patient. The disclosed dental repositioning appliances may comprise one or many integrated sensors. The disclosed dental reposition appliances, such as aligners, may comprise a change indicator system. The sensor or indicator system may be used to qualitatively or quantitatively monitor the corrective or repositioning force applied by the appliance. In some cases, the sensor or indicator system may provide a signal to patient that it is time to change the aligner when the current aligner no longer provides significant repositioning force. In some instances, the disclosed dental appliances may be utilized to collect data on the rate of tooth movement along a specified direction vector. In some instances, the disclosed dental appliances may be utilized to determine if one or more previous cycles of aligner wear have resulted in a position for one or more teeth that are off-target. In some instances, the disclosed dental appliances may be used to determine if the applied corrective force is too high, such that it may damage a tooth or the underlying ligaments.

In some cases, a dental appliance may comprise a removable aligner of the present disclosure. The appliance may include tooth receiving cavities shaped to receive the tooth of a patient therein and apply a repositions force to the tooth when the appliance is worn by the patient. The dental appliance may additionally comprise one or more sensors positioned adjacent to one or more teeth when the dental repositioning appliance is worn by a patient. The one or more sensors may collect comprise stress data, strain data, displacement data, etc. Mechanical stress in the material of the dental appliance, e.g., when the appliance is in place over the patient's teeth, may serve as an indicator of the repositioning force applied against the teeth. In some instances, stress/strain detection may be performed using one or more strain sensors or sensor films. The sensors may relay the data as described further in the section "Sensor Signal Processing".

In some instances, the disclosed dental repositioning appliances comprising sensors for monitoring the corrective force applied by the appliance may comprise one or more sensors. In some instances, the disclosed dental repositioning appliances may comprise at least one sensor, at least two sensors, at least three sensors, at least four sensors, at least five sensors, at least six sensors, at least seven sensors, at least eight sensors, at least nine sensors, at least ten sensors, at least twelve sensors, at least fourteen sensors, at least sixteen sensors, at least eighteen sensors, at least twenty sensors, or more. The dental appliance may comprise one or more different types of sensors. In some cases, the sensors may be all of the same type. In some cases, the appliance may comprise two or more different types of stress/strain sensors.

The sensors may be located on various portion of the appliance. The sensor may be near a distal portion, near a medial portion, near a buccal portion, near a lingual portion, near a gingival portion, near an occlusal portion, or a combination thereof. The sensor may be near a single tooth or near a portion of a single tooth. The sensor may be in between two teeth. The sensor may cover multiple teeth. The sensor or sensor array may cover an entire surface (interior or exterior) of an aligner.

In some embodiments, one or more sensors or parts of sensors may be placed directly on a tooth or teeth and others sensors or parts of the sensors may be placed on or in the aligner or other device such as a palatal expander. For example, a magnet may be attached to a person's tooth and a magnetometer may be located with the aligner. Thus, as the teeth move and/or as the aligner changes shape a distance or arrangement between the magnet and the magnetometer may change, and this change may be used to determine patient compliance with wearing the aligner, movement of the tooth, or effectiveness of the aligner, e.g., whether it is till applying a movement force to the aligner.

As another example, a conductive foil or other conductive material may be placed on a tooth surface and second foil may be located on or in the aligner, so it is incased in an insulator or an insulator is between the first and second foil. In such an example, the capacitance may be measured once the aligner is on the tooth as a compliance indicator possibility. In addition, the capacitance between the first and second foil may change as the tooth moves and/or the aligner material relaxes. In such embodiments, the changes in capacitance may indicate that less compressive force against the tooth is measured (e.g., as a lower capacitances). In some embodiments, a correlation between movement of a tooth or teeth in general and capacitance, magnetic field, or other sensor measurements between sensors on a tooth and on an aligner may be determined. Then, based on this correlation, tooth movement may be determined.

Any of a variety of sensors and sensing mechanisms known to those of skill in the art may be used to sense the level of repositioning forces or track the rate of tooth movement in implementing the disclosed methods and devices. Examples include, but are not limited to, the use of embedded stress/strain sensors and the use of capacitive sensing arrays. Other examples include piezoelectric strain sensors, nanoparticle-based strain sensors, optical strain sensors, and capacitive sensing array sensors. In some instances, the strain sensors may be microscale strain gauges, e.g., piezo-resistant strain gauges. In some instances, the strain sensors may be nanoparticle-based strain sensors, which comprise an assembly of conductive nanoparticles such as gold and carbon nanoparticles, and have a large deformation range and a low electrical requirement. In some examples, the sensor may be placed in areas of predicted stress or strain such as between appliance cavities. The sensors may be uniformly distributed through the appliance.

In cases where the sensor is electrical, the appliance may comprise a voltage and/or current sensor within the appliance. In some cases, a small voltage may be applied to the sensor. The appliance may comprise an insulating material to limit exposure of a patient to electricity from the sensor. The electrical circuit may comprise a Wheatstone bridge, a chevron bridge, etc. The appliance may comprise a power supply such as a battery to power the sensor. The appliance may comprise a microscale processor to perform operations such as transmit data, turn on/off the sensor, etc. The appliance may comprise a barrier to limit patient exposure to sensor materials such as heavy metals or nanomaterials. For example, in some instances, the stress/strain sensors may comprise an insulating flexible backing which supports a patterned array of sensors. In some cases, the sensor array may be attached to a surface of the dental appliance using an adhesive; however, the sensor array may be manufactured within appliance. As the appliance is deformed by positioning over the teeth, the pattern may be deformed causing its stress and/or strain to change.

In some instances, the stress/strain sensors may be piezoelectric sensors, which can measure a change in strain by converting it to an electrical current. Stress and/or strain in the piezoelectric material may be related to a change in a potential measured by electrical leads in the dental appliance. In some cases, the relative magnitude of either the voltage or rate of change of voltage generated by the sensor may be measured. The appliance may include a material that is piezoelectric. The piezoelectric material may be a piezofilm. The piezoelectric material may be a piezoceramic. The piezoelectric material may be gallium phosphate, quartz, tourmaline, Magnesium Niobate-Lead Titanate (PMN-PT), or any other suitable piezoelectric material. A piezoelectric sensor may operate in a transverse, longitudinal, or shear mode.

In some cases, the stress/strain sensors may be piezoresistive sensors. Rather than effecting the voltage, stress or strain in the system may be related to a change in the resistance measured by electrical leads in the dental appliance. The relative magnitude of the resistance or the rate of change of the resistance may be measured. The appliance may be constructed from a material that is piezoresistive. The piezoresistive sensor may comprise silicon, germanium, or an alloy of silicon and germanium. The piezoresistive sensor may comprise carbon nanotubes, fullerenes, or diamond. The piezoresistive sensor may comprise silicon carbide. The piezoresistive sensor may comprise an array of nanowires, such as p-type silicon nanowires. The piezoresistive sensor may comprise any suitable piezoresistive material.

Figure 4A:
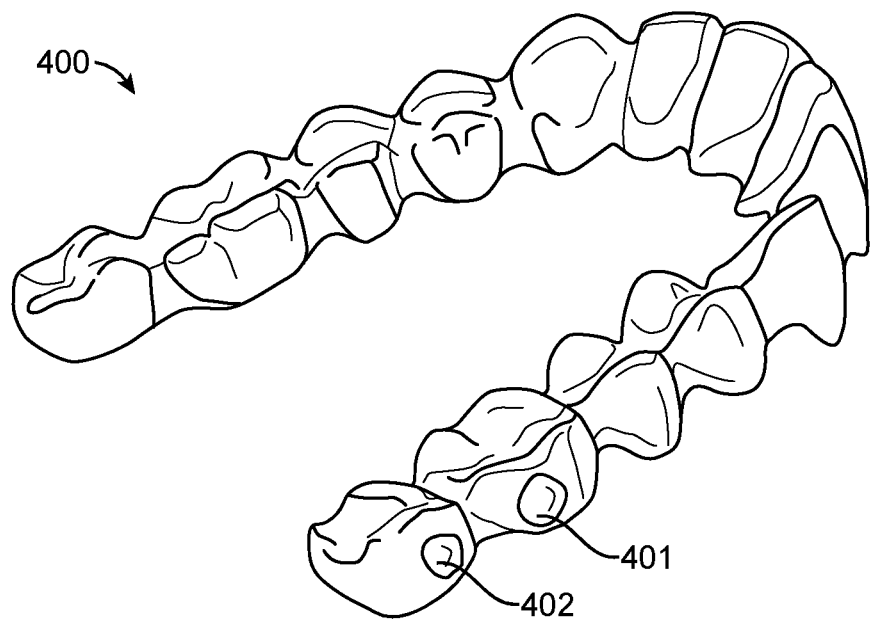
FIGS. 4A-E provide a non-limiting example of the placement of stress/strain sensors relative to a patient's teeth.
Figure 4B:
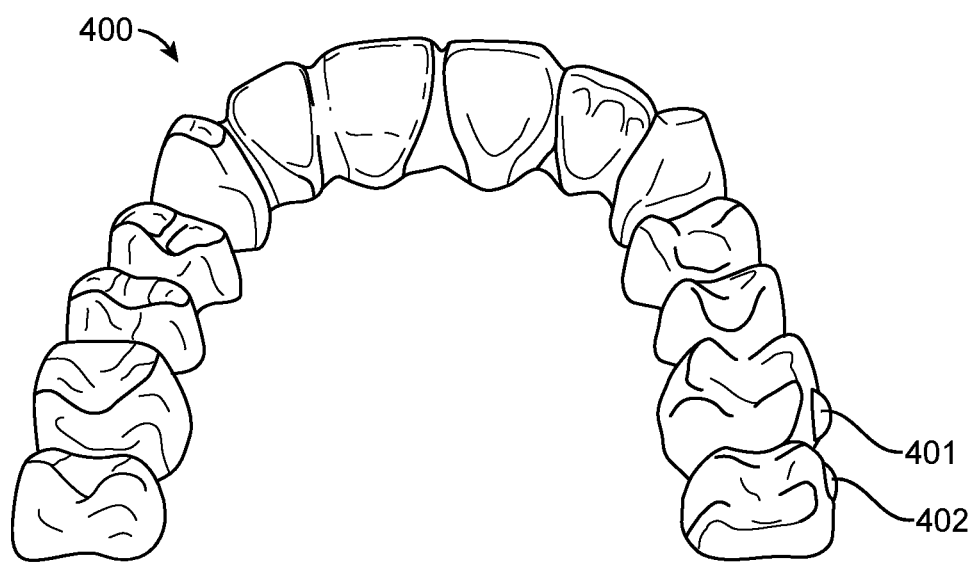

FIG. 4A provides an isometric view of a dental appliance of the present disclosure comprising two stress/strain sensors. A first sensor 401 may be positioned on the appliance 400 so that it is adjacent to the tooth that is to be repositioned through use of the aligner. A second sensor 402 may be positioned on the appliance so that it is adjacent to the neighboring tooth. In some cases, the second tooth may be more or less stationary. In some cases, the individual sensors may be placed at a region of interest, such as a location of maximal strain. The sensors may be placed at the location of a leading tooth. FIG. 4B shows a partial occlusal view of the same dental appliance. Piezoresistive and piezocapacitive sensors of the present disclosure may generally take the form of sensors 401 and 402. Sensor 401 may be a sensor on an exterior surface of a tooth. Sensor 402 may be a sensor placed at a local stress point on an aligner.

Figure 4C:
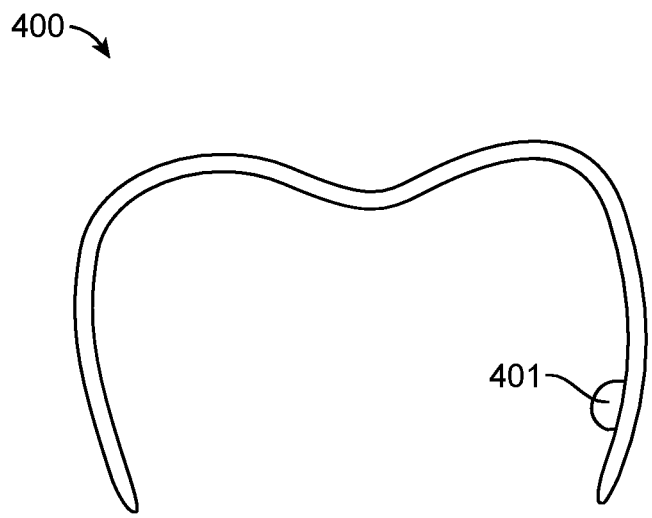

FIG. 4C provides a cross section through a dental appliance of the present disclosure comprising a stress and/or strain sensor on an interior surface of an appliance. In the illustrated embodiment, appliance 400 may comprise a sensor 401 on an interior of the appliance. In some cases, the sensor 401 extends above the interior surface of the appliance; however, the sensor 401 may be recessed within the body of the appliance or partially recessed within the body of the appliance. In some cases, the sensor 401 may be flush with the interior surface of the appliance.

Figure 4D:
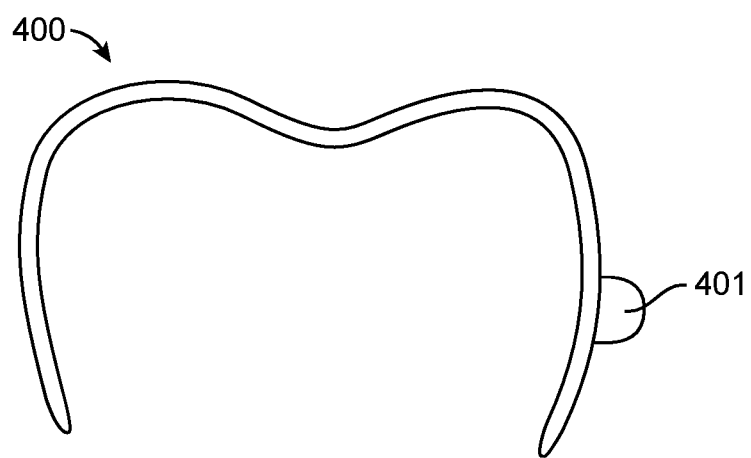

FIG. 4D provides a cross section through a dental appliance of the present disclosure comprising a stress and/or strain sensor on an exterior surface of an appliance. In the illustrated embodiment, appliance 400 may comprise a sensor 401 on an exterior of the appliance. In some cases, the sensor 401 extends above the exterior surface of the appliance; however, the sensor 401 may be recessed within the body of the appliance or partially recessed within the body of the appliance. In some cases, the sensor 401 may be flush with the exterior surface of the appliance.

Figure 4E:
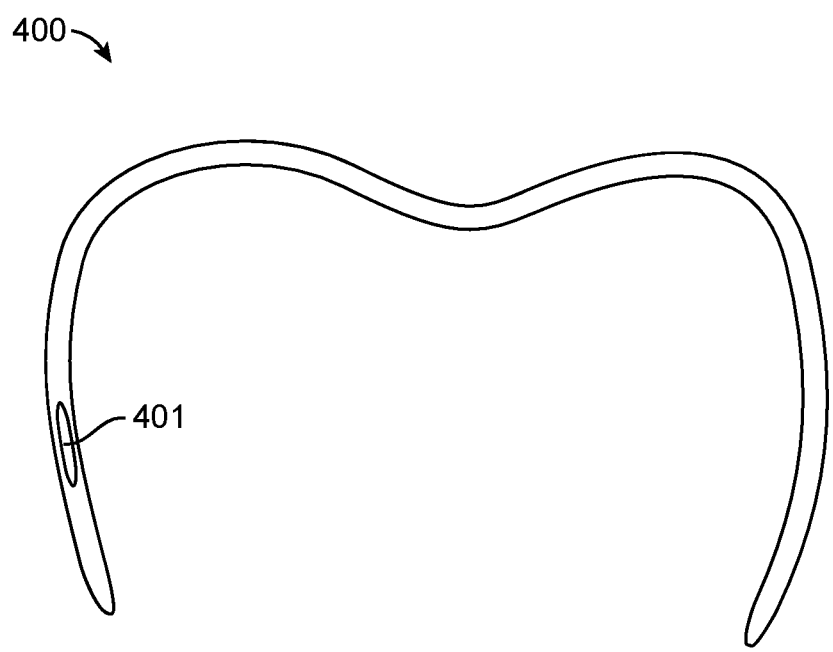

FIG. 4E provides a cross section through a dental appliance of the present disclosure comprising a stress and/or strain sensor inside the body of an appliance. In the illustrated embodiment, appliance 400 may comprise a sensor 401 on within the body of appliance 400. The appliance may be thicker to accommodate a sensor. In some cases, sensor 401 may be in the form of an elongated sheet. Placing the sensor within the body of the appliance may reduce patient exposure to the sensor device. Placing the sensor within the body of the appliance may reduce exposure of the sensor device to, for example, food and patient saliva. In some embodiments, the appliance comprises a thermoformed multilayer material. For example, the multilayer material may be multilayer sheet of material or multiple sheets of material. The sensor may be placed between layers of the sheet or material.

In some cases, the stress/strain sensor may be a capacitive stress/strain gauge. A capacitive strain gauge may comprise one or more pairs of conductors spaced apart from one another. They can be separated by an air gap or by an electrical insulator. A change in the relative distance of the two conductors may change the capacitance of the system. The relative magnitude of the capacitance or the rate of change of the capacitance may be measured. In some instances, the dental appliance may comprise sensors which make up a capacitive sensing array that relies on capacitive coupling to detect deformation by measuring changes in capacitance. The sensors in the capacitive sensing array can be made of, for example, copper, indium tin oxide, carbonnanotubes, graphite, silver, or printed ink. The sensors in the capacitive sensing array may be mutual capacitance sensors or absolute capacitance sensors.

Figure 5A:
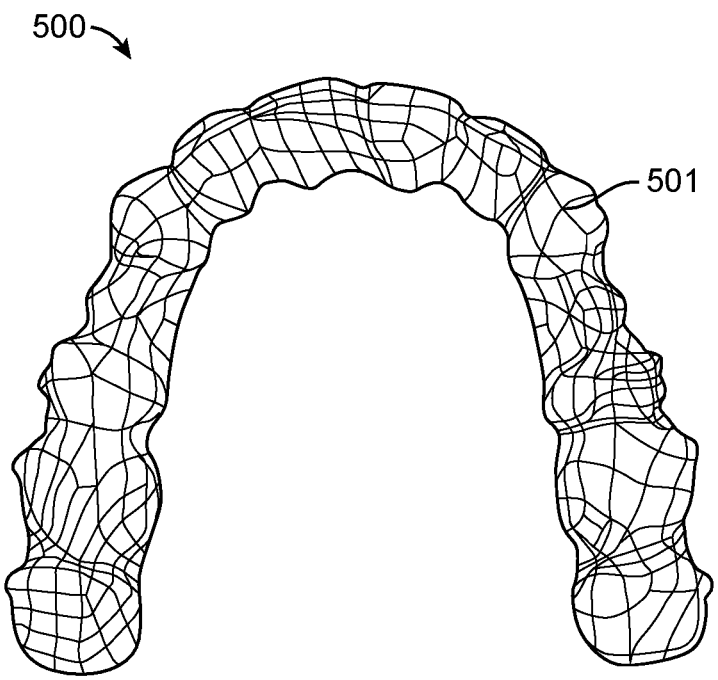
FIGS. 5A-E provide a non-limiting example of the placement of microfluidic channels within a dental appliance.
Figure 5B:
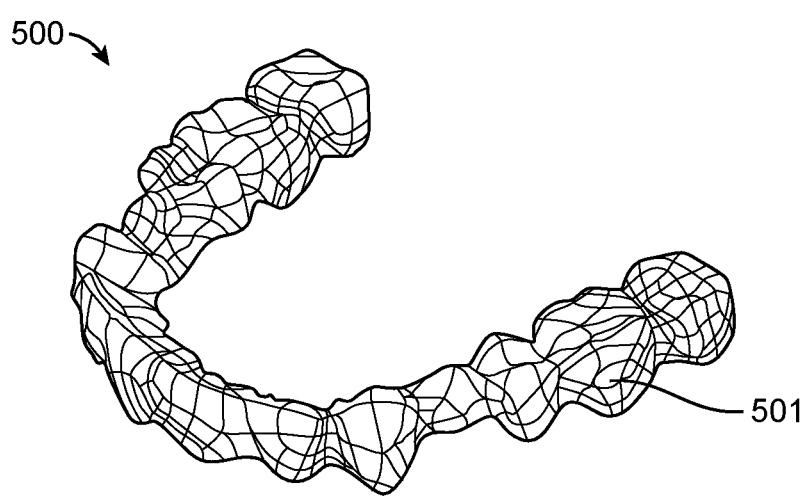

FIG. 5A provides a top view of a dental appliance of the present disclosure with a capacitive sensing array. The capacitive sensing array may comprise embedded microfluidic channels 501 that may be filled with a liquid metal alloy such as eutectic Gallium-Indium or other conductive fluid to create a capacitive sensing array to measure local stress/strain. FIG. 5B provides an isometric view of the same appliance. In some instances, a dental appliance 500 may be embedded with microchannels 501 filled with a liquid metal alloy to create soft electronic sensors that detect deformation by measuring changes in capacitance. The capacitance of the liquid conductor can be measured at different locations to gain information about stress/strain and potential stress vectors that are present in multiple locations of the aligner. One non-limiting example of a liquid metal alloy that is suitable for use in a direct filament casting process is eutectic gallium indium (eGaIn) comprising 75% Ga and 25% in by mass (melting point=15.7 C). The eutectic gallium indium may comprise Gallium within a range from 50% to 99% by weight. The eutectic gallium indium may comprise Indium within a range from 1% to 50% by weight. The eutectic gallium indium may comprise other materials such as dopants and/or trace metals in addition to Gallium and Indium. The eutectic gallium indium may comprise Tin at less than 20% by weight. The ratio of the various components may be further limited by the range in which eutectic gallium indium may remain eutectic. The channels may be sealed to prevent patient toxicity.

Figure 5C:
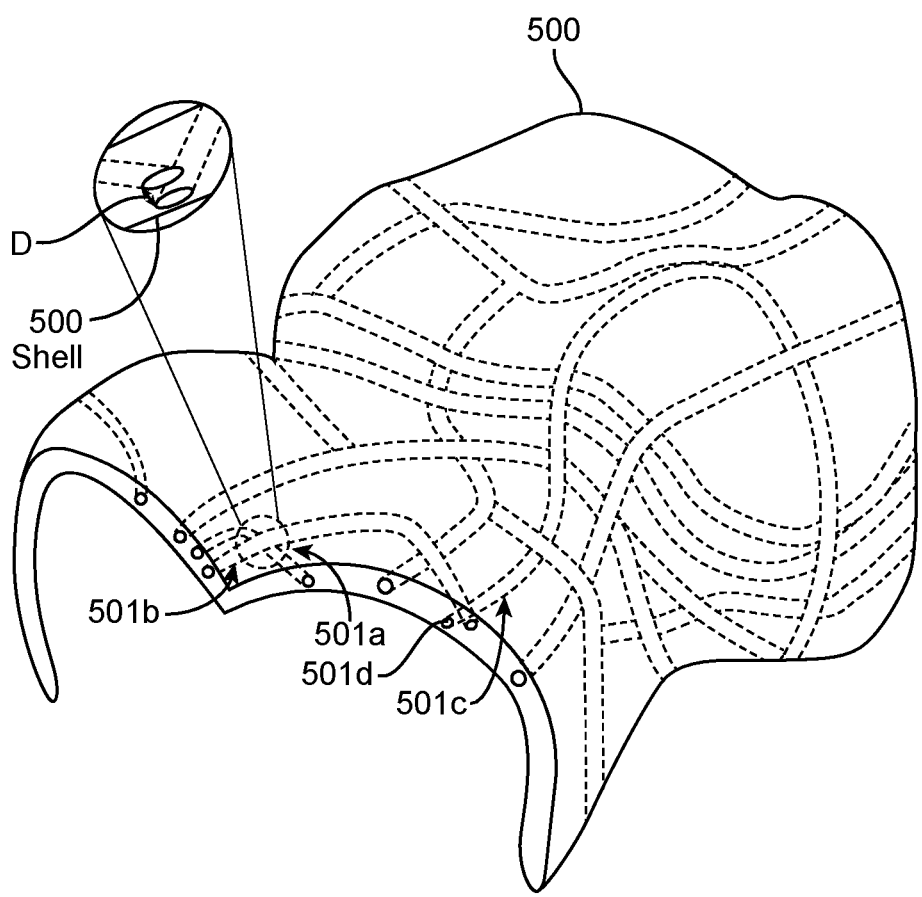

FIG. 5C provides a transparent view of a dental appliance of the present disclosure with a capacitive sensing array. FIG. 5C shows microfluidic channels 501*a*, 501*b*, 501*c*, and 501*d* within the body of the appliance 500. In some cases, the microfluidic channels may be imbedded within the body of the shell. The microfluidic channels may be sufficiently thin such that the shell does not bulge at the locations of the channels. The interior surface of appliance 500 may be smooth. The exterior surface of the appliance 500 may be smooth. In some cases, the channels may be transparent. The channels within the appliance may overlap at locations 502, such as locations 502*a* and 502*b*. FIG. 5C shows an inset with a slice through the appliance. As shown in the inset, the channels may be separated by an interior distance D. As shown in the inset, in some cases, each channel may comprise fluid which is isolated from any other channel. In some embodiments, the microfluidic channels may intersect. For example, where the microfluidic channels intersect, the fluid from one channel may flow freely into an intersecting channel. At multiple locations along the channels or at a channel terminus, the capacitance between two or more channels may be measured. For example, a conductive lead or other device may connect to the channels at measurement locations. The system may then measure and distinguish the capacitance between the channels at the multiple locations.

Figure 5D:
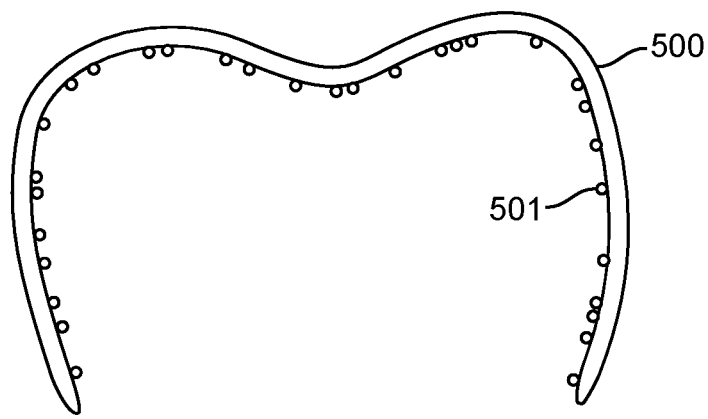

FIG. 5D shows an appliance 500 with microfluidic channels on an exterior surface of the appliance. The microfluidic channels may be sealed from the patient oral cavity. The microfluidic channels may resist compression, such as from a patient bite. Though FIG. 5D shows microfluidic channels on the interior surface of an appliance, a stress and/or strain gauge of the present disclosure is envisioned on an interior surface of an appliance as shown in FIG. 5D. However, even if the patient bites the aligner and imposes a stress/strain measured by the sensor, such measurements can be averaged out or seen as transitory and thus the actual stress/strain caused by the fitting of the aligner on the teeth (and not from the bite nor other interferences) can be determined.

Figure 5E:
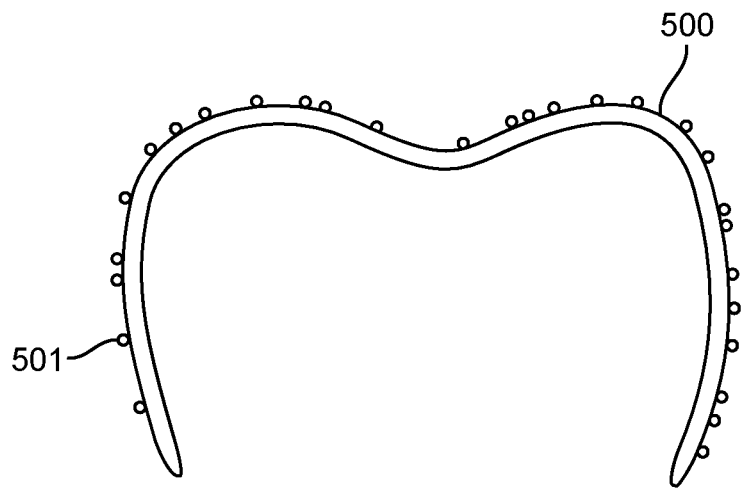

FIG. 5E shows an appliance 500 with microfluidic channels on an interior surface of the appliance. The microfluidic channels may be sealed from the patient oral cavity. Though FIG. 5E shows microfluidic channels on the exterior surface of an appliance, a stress and/or strain gauge of the present disclosure is envisioned on an exterior surface of an appliance as shown in FIG. 5E.

In some cases, the stress/strains sensor may be an inductive stress/strain gauge. The force or the torque due to deformation on an inductor may affect the current flowing through the inductor. The relative magnitude of the inductance or the rate of change of the inductance may be measured.

In some cases, the stress/strain sensor is a metal foil strain gauge. For example, in some instances, the stress/strain sensors may comprise an insulating flexible backing which supports a metallic foil pattern. Without being limited by theory, when an electrical conductor is stretched within the limits of its elasticity such that it does not break or permanently deform, it may become narrower and longer, which increases its electrical resistance end-to-end. In some cases, a small potential may be applied during measurement. The potential may be less than 15 Volts, less than 5 Volts, less than 1 volt, less than 100 millivolts, less than 1 millivolt, or less. A foil strain sensor may be attached to a surface of the dental appliance using any suitable adhesive. As the appliance is deformed by positioning over the teeth, the foil may be deformed thereby causing its electrical resistance to change. A similar change in resistance my result from a microchannel filled with a conductor (liquid or solid) as well. Very thin conductive wires embedded into the aligner are an example of a solid microchannel filled with a solid conductor. Salt water inside micro channels are a non-limiting example of a liquid conductor. Such conductors can be embedded into the aligner and/or adhered to the surface. The electrical resistance of the conductor is measured.

In some cases, the stress/strain sensor is a nanoparticle strain sensor. The nanoparticle strain sensory may comprise metallic nanoparticle assemblies positioned between two conductive electrodes. Without being limited by theory, the resistance of the nanoparticle strain sensory may be related to changes in current tunneling through nanogaps present between nanoparticles. The nanoparticles may comprise silver nanoparticles, gold nanoparticles, and/or platinum nanoparticles. The nanoparticles may comprise metallic nanoparticles. The nanoparticle may comprise carbon nanoparticles. The electrodes may comprise any suitable conductor. In such instances, the connectivity of the conductors across the length of the material may be affected by minor movements in the material and as such the resistance can change based on these minor movements. The minor movements may result in large changes. Such environmental effects such as moisture and/or temperature changes can be filtered out. It is also understood that the nanoparticles can be nanowires or other shapes. For example, metallic carbon-nanotubes can be arranged to form a conductive network at a concentration that renders them greater than 90% transparent. Note that the latter arrangement may use fully organic materials and without metals. Nano-sized devices aid in the transparency of the aligner and the likelihood that such devices will not be readily visually apparent to the user and the people the user interacts with. It is also anticipated that larger particles, wires, and/or other shapes that comprise the loosely connected network of conductors can be any size that creates a functional sensor within an aligner.

In some cases, the stress/strain sensor may include a plurality of electrodes, such as sensor legs. The sensor may be configured to sense a distance between two or more of the plurality of legs and to identify a spatially distributed strain on the region of an aligner based on the sensed distance.

In some cases, the stress/strain sensor is an optical stress/strain sensor. In some instances, the strain sensors may be optical strain sensors, e.g., fiber optic strain sensors which rely on modifying a fiber so that the quantity to be measured modulates the intensity, phase, polarization, wavelength or transit time of light in the fiber. In some instances, the strain sensors may be microscale strain gauges, e.g., integrated optical ring resonators. In some instances, a reflective material may be applied on the lingual surface of anteriors and buccal surface of posteriors after the aligner is fabricated. While patients are wearing the aligners, a portable polarized light source can be placed in the patient's mouth and stabilized in a fixed position to record birefringence patterns, thus comparing stress in the aligners.

In some cases, the stress/strain sensor is a magnetic stress/strain sensor. The stress/strain sensors may comprise a magnetometer and a magnet separated by a given distance. If the distance changes, the magnetometer can detect the change and can determine a strain. There are lots of different magnetometers that could potentially be used. A non-limiting example of a small magnetometer is a MEMS magnetic field sensor which is a small-scale microelectromechanical systems (MEMS) device for detecting and measuring magnetic fields. When a magnetometer is used on an aligner, a magnet (and sometimes even a ferrous metal) can be placed nearby. Changes in the distance between the magnetometer and the magnet are measured by the magnetometer (by calibration of the magnetometer signal and the distance to the magnet).

The one or more sensors may be attached to a surface of the dental appliance or embedded within the dental appliance. If it is attached to a surface (or to a feature of the appliance surface designed to mate with the sensor), it may be attached, e.g., using an adhesive or a snap-to-fit mechanism. In some instances, a sensor may be inserted into the polymeric material of the dental appliance as the appliance is being fabricated, i.e., while the polymer is still above its glass transition temperature. In some instances, it may be directly 3D printed within the appliance, micro-molded within the appliance, or inserted during assembly of the appliance.

A stress/strain sensor may be operably coupled to the appliance in a variety of ways. For example, the monitoring sensor can be physically integrated with the appliance by coupling the stress/strain sensor to a portion of the appliance (e.g., using adhesives, fasteners, latching, laminating, molding, etc.). The coupling may be a releasable coupling allowing for removal of the stress/strain sensor from the appliance, or may be a permanent coupling in which the stress/strain sensor is permanently affixed to the appliance. Alternatively or in combination, the stress/strain sensor can be physically integrated with the appliance by encapsulating, embedding, printing, or otherwise forming the stress/strain sensor with the appliance. In some embodiments, the appliance includes a shell shaped to receive the patient's teeth, and the stress/strain sensor is physically integrated with the shell. The stress/strain sensor can be located on an inner surface of the shell (e.g., the surface adjacent to the received teeth), an outer surface of the shell (e.g., the surface away from the received teeth), or within a wall of the shell. Optionally, the shell can include a receptacle shaped to receive the stress/strain sensor.

In some instances, the sensors may be arranged in a pattern forming a mesh or an array. The pattern in which the sensors are arranged may be random or geometric. The pattern in which the sensors are arranged may be consistent across the entire dental appliance, or the pattern may differ at different locations on the dental appliance. The sensors may be interconnected, independent of one another, or a series of independent sets of interconnected sensors.

When a custom dental repositioning appliance (or "aligner") is ready to be designed and fabricated, the patent identification (PID) file may provide information about which tooth/teeth are providing the maximum force. The stress/strain sensor/films may be embedded on or close to the target tooth/teeth to collect stress/strain data. In some cases, the density of sensing elements may be increased near areas of high strain during manufacturing of the appliance. The PID file may be updated with information from the stress/strain sensors as the stress/strain changes. The PID file may contain a log of the sensor data, which may be provided to a health care provider.

At the same time, the sensor(s) may send a signal to an application installed on a patient's cellphone. When the stress/strain value is close to zero due to material stress relaxation, a reminder to change to the next aligner in the series included in the treatment plan may be provided to the patient.

Systems and method described herein may be combined with Electronic Compliance Indicator (ECI) apparatuses that may be configured to record sensor data from subjects (e.g., patients) wearing or intended/intending to wear an orthodontic aligner such as a shell aligner.

Figure 7:
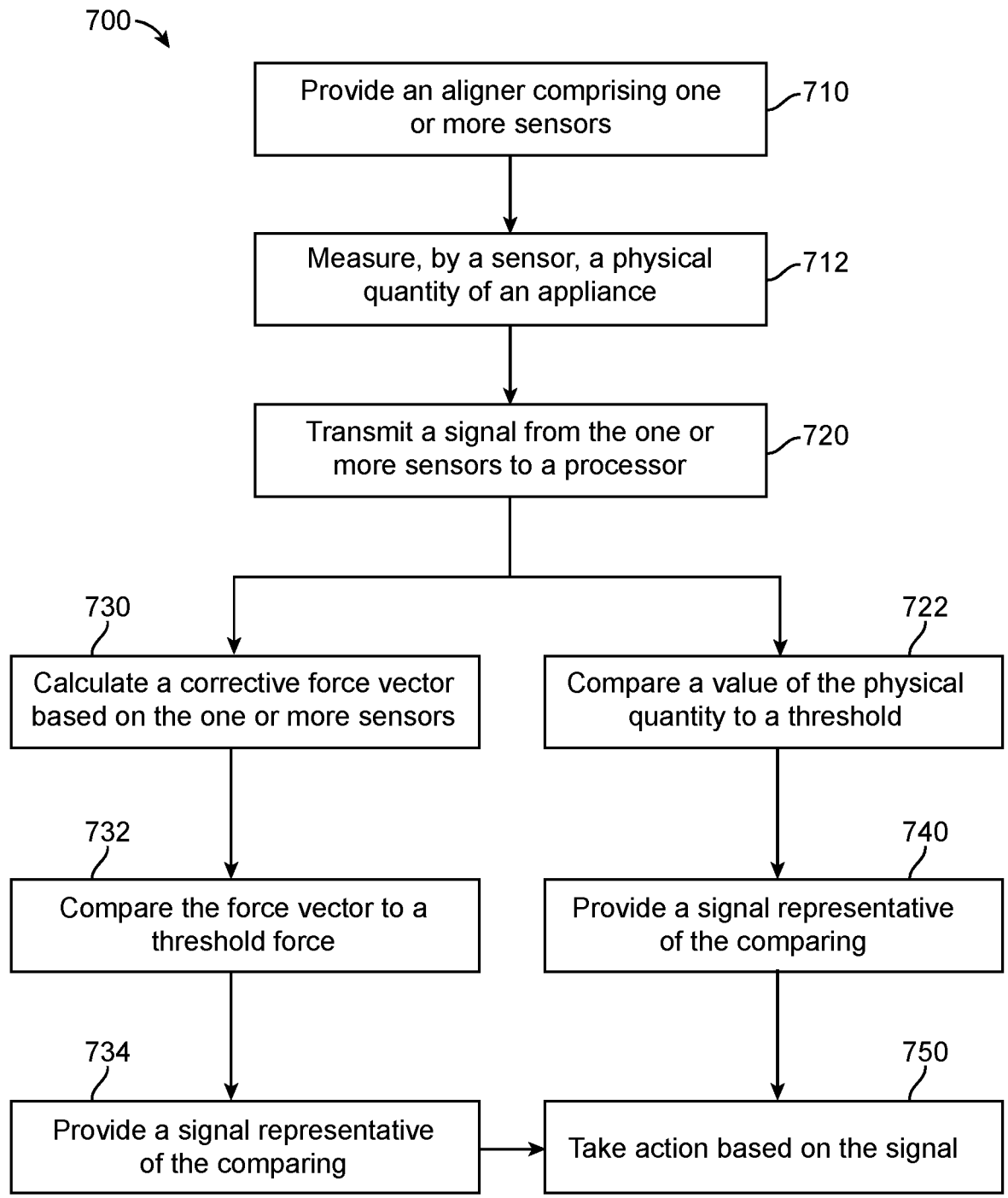
FIG. 7 shows a method of quantifying corrective force, in accordance with one or more aspects of the methods disclosed herein.

As shown in FIG. 7, the present disclosure may provide methods for quantifying a corrective force applied to a patient's teeth. The force may comprise the force from a dental appliance. The force may comprise the force from an attachment to a positioning alliance. Methods of the present disclosure may comprise any embodiment of the appliance with a sensor provided herein. The sensor may be adjacent to one or more of a patient's teeth. The appliance may generally conform to the shape of the patient teeth; however, the appliance may resist conformation such that the aligner provides a repositioning force to the patient teeth as described elsewhere herein. The appliance may be worn by a patient.

At an operation 710 of the method 700, a dental appliance comprising one or more sensors positioned adjacent to one or more teeth may be provided. The dental appliance may be one of a plurality of dental appliances to effectuate the steps of a treatment plan. The treatment plan may be determined before operation 710. In some cases, the treatment plan may be generated or modified based on the sensor data. Sensor data may be collected substantially continuously.

At operation 712 of the method 700, the sensor may measure a physical quantity of a region of the dental appliance to generate sensor data. The sensor may be an embedded sensor that is embedded into a region of the first aligner. The dental appliance may be an aligner that moves one or more teeth for a treatment stage of an orthodontic treatment plan. The physical quantity measured and the sensory data generated may include stress data, such as the material stress, strain data, such as the material strain, displacement data or movement data, such as movement of a region of an aligner between a relaxed position and a deformed position, or any combination thereof. In some cases, the physical quantity may be measured and the sensor data may be collected once a treatment phase, once a week, once a day, once an hour, every minute, every second, every millisecond, or even more frequently. Sensor data may be collected over a period of time and then terminated. The frequency of sensor data collection may be adjusted using a processor as described elsewhere herein.

In some embodiments, the sensor includes one or more microfluidic channels, such as those described with respect to FIG. 5 and elsewhere herein. In such a sensor, a capacitance of a region between microfluidic channels and the substance therein is sensed. The sensed capacitance may be indicative of a spatially distributed strain on the region of the aligner and the strain, or an indication of the amount of strain, in the region may be determined based on the sensed capacitance.

In some embodiments, a sensor is placed on or in the appliance at a location corresponding to a tooth receiving cavity of a leading tooth. In some embodiments, the region corresponds to a leading tooth receiving cavity. In some embodiments, the region may include one or more tooth receiving cavities. In some embodiments, the region may span more than one tooth receiving cavity. In some embodiments, the region may be distributed about the aligner.

The functionality of the sensor is discussed further in the section "Sensor Signal Processing".

At an operation 720 of the method 700, one or more signals generated by the one or more sensors may be transmitted to a processor. The processor may be an external signal processor. The processor may be a cell phone, a tablet, a personal computer, or other processor as described elsewhere herein. The signal may be transmitted via Bluetooth, via Wifi, or via any suitable electromagnetic transmission. The sensor data may be processed on an internal microprocessor. In some cases, the sensor data may be processed on an external microprocessor. The sensor data may be stored on board. The sensor data may be stored locally on a cell phone, a laptop computer, a personal computer, or a computer system. The sensor data may be stored in a cloud-based database. The sensor data may be transmitted to an external processor such as the processor of a health provider, a cloud computing system, a cell phone, or any other processor described herein. The transmitting may be performed substantially continuously. The transmitting may be performed at regular intervals. The transmitting may be performed periodically. The transmitting may occur at random intervals. The transmitting may be performed discontinuously. The transmitting may stop for a period or transmit in bursts. The transmitting may occur during data collection in between periods of data collection or both.

At an operation 722 of the method 700 a value of the physical quantity is compared to a threshold. The threshold may be determined in advance. The threshold may correspond to a particular force or reduction in force applied to the teeth in accordance with a stage of the treatment plan. The comparing may include a determination whether the value of the physical quantity is greater than or less than the threshold. In some embodiments, the threshold is associated with a relaxation of the aligner and the material that makes up the aligner. The comparing may compare the sensed relaxation of the aligner with a threshold relaxation that, for example, indicates that the aligner is relaxed to a degree such that it no longer provides repositioning forces to the teeth of the patient.

At an operation 740 of the method 700 a signal is provided that represents a result of the comparing. For example, the signal may be an electrical signal indicating that the stage is complete or to change to the next appliance in the treatment plan.

At an operation 730 of the method 700, a corrective force may be calculated. The corrective force may be based on one or more signals transmitted from the sensors. The corrected force may be based on the position of the one or more sensors. From the sensor data, the rate of movement of one or more teeth may be calculated.

At an operation 732 of the method 700 the rate of movement or the force vector may be compared to a target rate of movement from a treatment plan or a threshold force and at operation 734 a signal representative of the comparing may be transmitted. The calculated value of the corrective force may be used to determine when the dental appliance should be removed or replaced.

At an operation 750 of the method 700 may comprise providing a subsequent appliance after a measurement of the corrective force. An operation of the method 700 may comprise modifying a treatment plan based on the corrective force. An operation of the method 700 may comprise advising a patient to discontinue using an appliance based on a corrective force. An operation of the method 700 may comprise modifying a treatment schedule for a patient. The calculated corrective force may be compared to known safe levels of alignment. The force may be transmitted to a health provider to update the treatment plan remotely. The force may be transmitted to a secure server. The force may be logged for later analysis.

At operation 750 a prescribed duration for wearing an aligner may be determined based on the treatment plan. In some embodiments, the time between the initial application of an appliance and when the sensor indicates the appliance is no longer effective, an effective time, is determined. The effective time may be based on a specified reduction in force, relaxation, stress, or strain of the appliance when applied to the teeth. In some embodiments, a determination is made as to whether to or not the prescribed duration has been met.

In some embodiments, at operation 750, a recommendation is made to accelerate treatment and advance to a next stage of treatment when the effective time is less than then prescribed duration. For example, when the effective time is determined to be within a threshold amount of the prescribed duration, such as greater than 90% or 95% of the prescribed duration, but less than 100%, then the patient may advance to the next stage of treatment. In some embodiments, a recommendation is made to advance to a next stage of treatment without regard to the effective time. In some embodiments, an indication that an appliance is no longer effective indicates that the patient should move to the next stage of treatment by applying the next aligner. In some embodiments, at operation 750, a recommendation is made to prolong treatment and advance to a next stage of treatment when the effective time is greater than then prescribed duration. For example, when the effective time is determined to be greater than a threshold amount of the prescribed duration, such as 110% or 105% of the prescribed duration, then the patient may advance to the next stage of treatment.

Figure 8:
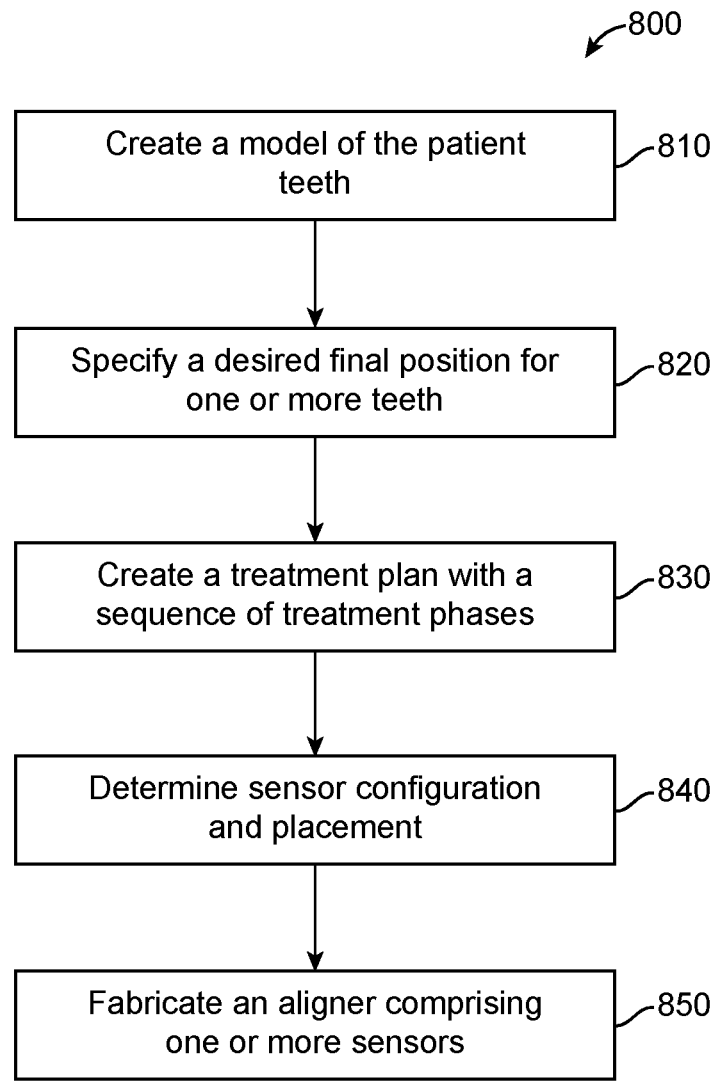
FIG. 8 shows a method of designing a dental appliance, in accordance with one or more aspects of the methods disclosed herein.

As shown in FIG. 8, the present disclosure provides a method for designing an orthodontic appliance. Methods of the present disclosure may comprise an appliance with a sensor provided herein. The sensor may be adjacent to one or more of a patient's teeth. At an operation 810 of the method 800, a model of the patient's teeth may be provided. The model may be provided based on a scan of the patient teeth. The model may be provided based on a mold of a patient's teeth. The model may be a physical model. The model may be a 3D model. The model may comprise a 3D scan or a 2D scan. The model may be digitized with the aid of a processor. The operation 810 may comprise one or more operations of the method 300 as described herein.

At an operation 820 of the method 800, a desired final position for a one or more teeth may be provided. The final position may be the desired position at the end of a stage of a treatment plan or at the end of a treatment plan. The final position may be based on a digital model of the patient teeth. The operation 820 may comprise one or more steps of the method 200 as described herein.

At an operation 830 of the method 800, a treatment plan may be created. The treatment plan may comprise a sequence of steps or stages for repositioning one or more teeth. For example, the treatment may comprise one or more steps or stages to move the teeth towards a desired position. The desired position may be the desired final position of the teeth after treatment. Creating a treatment plan may comprise identifying one or more teeth with a high rate of movement. The treatment plan may comprise identifying the tooth with the highest rate of movement. The treatment plan may comprise identifying the tooth with the highest level of torque. The treatment plan may comprise identifying one or more teeth with a high level of torque. A level of torque may be high relative to the rest of the teeth. A level of torque may be high relative to a specified torque for a treatment plan. A level of torque may be high relative to safe levels. The treatment plan may be modified based on a stress and/or strain measured from a sensor.

At an operation 840 a sensor configuration is determined. In some embodiments, the treatment plan is accessed and an aligner for a stage of treatment of the treatment plan is identified or otherwise determined. A region of an aligner may be identified for tracking an aligner physical quality. The region may correspond to a leading tooth or a tooth receiving cavity of a leading tooth of an arch of a patient. The physical quality of a region of the first aligner may be correlated with a force applied by the aligner during the stage of the treatment plan. In some embodiments, a threshold value of the physical quality is identified. The threshold value may correspond to a reduction in the force to the teeth applied by the aligner to the leading tooth during the stage of the treatment plan. The leading tooth may be a tooth that moves a greater distance or at a greater rate than the other teach of the patient during the stage of treatment.

At an operation 840 a sensor configured to sense the physical quality is selected. During treatment, the sensor may aid in determining that the physical quality falls below or otherwise crosses a threshold value.

At an operation 850 of the method 800, an appliance with a stress/strain sensor may be fabricated. The appliance may be fabricated by any of the methods described herein, for example, one or more appliances are fabricated using a fabrication machine, such as fabrication machine 622, accordingly to one or more fabrication processes or methods described herein. The sensor may be fabricated in or on the appliance such that when the appliance is worn by the patient, the sensor contacts one or more of the patient teeth. The sensor may be located on or in the appliance at a location adjacent to a tooth receiving cavity. A sensor may be placed on or in or otherwise coupled to the appliance such that it is adjacent to each tooth to be repositioned when the appliance is worn by the patient. The one or more sensors may be adhesive backed sensors. The sensors may be adhered to a surface of a repositioning appliance. The sensor may be adhered to a surface of a repositioning appliance which has been directly fabricated. The sensor may be inserted into a polymer aligner which has been heated above the glass transition temperature. The sensor may be inserted into a pocket of an appliance that has been directly fabricated. After insertion of the sensor into the directly fabricated pocket, the additional appliance material may be formed over the sensor and the pocket to cover (i.e encapsulate) the sensor.

Sensor Signal Processing

Once the sensor data is acquired, it will be analyzed to determine the presence or absence of a repositioning force, such as a repositioning force sufficient to move a tooth. This can be achieved either by calculating the absolute value of local stress/strain and comparing it to a threshold value, or by calculating the change in stress/strain over time and comparing it to a maximum amount of change in stress/strain estimated for the appliance to be effective. This data can be analyzed for each tooth, averaged across a subset of teeth, or averaged for all teeth. The analysis may be the same for all patients, or it may be customized for an individual patient based on the amount of movement required for each tooth in that patient.

The system might also contain a sensor or network of sensors which track the position of one or more teeth relative to one or more other teeth. Data from a sensor may be analyzed to determine the movement rate of one or more of the teeth. When the movement rate is not within a specified window, the system will notify the patient or physician that the treatment schedule (i.e., the schedule for changing from one aligner to the next) may be altered. If the movement rate is higher than the maximum value in the specified window, then the teeth are moving too fast and the treatment schedule should be modified to slow the movement of the teeth. If the movement rate is lower than the minimum value in the specified range, the treatment schedule may be changed in order to speed up treatment, such as by applying more force.

Once the data is collected from the sensor, it may be analyzed. The data may be analyzed on a processor residing on a chip on the dental apparatus, on a cell phone, or on a processor at a remote computer (e.g., a laptop computer, a personal computer, or a computer system). Data analysis may occur at more than one of these locations.

Either the raw data or the analyzed data or both may be stored. The data may be stored directly on the sensor or within a circuit of the appliance, on the cell phone, and/or on a remote server at a remote computer. In some instances, the data may reside in a cloud-based database. The data may be stored at one or more of these locations at any given time, and may be stored either temporarily or permanently at each of these locations.

In some cases, the one or more sensors may be configured for wireless transmission. The one or more signals generated by the sensors may be transmitted to an external device such as a cell phone, a table, a laptop, an external serve, or any suitable processor. The sensor data may be analyzed on an external processing device. For example, the sensor data may be processed to calculate a corrective force vector. The corrective force vector may include data from the position of the one or more sensors. The corrective force vector may include data from a magnitude of the strain at the sensor. The external processor may calculate a rate of movement based on the one or more signals In order to ensure accuracy of the customized dental repositioning appliance and to allow optimal alterations to the treatment schedule, the appliance may also include a sensor which indicates apparatus wear. This may be a sensor which does not collect data, but rather provides an indication of whether the patient has been wearing the appliance, and may sense, for example, humidity, pH, temperature, vibration, or air flow. Alternatively, this may be a sensor which can collect data and send it to the computer where the tooth movement data is stored, such that the tooth movement data can be analyzed in view of the wear data, and may sense, for example, humidity, pH, temperature, vibration, or air flow. Inclusion of this sensor is not necessary for the system, but will allow for more accurate optimization of the treatment schedule. For example, the appliance will not be changed out early in response to a low strain signal if the low strain is due to a lack of wear of the appliance.

The dental appliance may include a power source to power any sensor or transmitter attached to the dental appliance. This power source can be a rechargeable battery, a non-rechargeable battery, or another power source. This power source will function to provide power to the sensors and transmission component.

Data Network

In some instances, the disclosed tooth repositioning systems (customized aligner change indicator systems) may comprise an application for a cell phone, may comprise an indicator (e.g., a wear indicator) directly on the dental appliance, or may comprise means for communicating with, and storing and analyzing data at, a remote computer comprising a server and a processor which are linked. In some instances, the cell phone application and/or remote computer may be accessed by the patient and/or physician to monitor the progress of treatment.

In some instances, the disclosed tooth repositioning systems (customized aligner change indicator systems) may comprise a means of communicating data from the aligner to the cell phone, which may then store and analyze the data. Data communication may be achieved using any of a variety of techniques and standards known to those of skill in the art including, but not limited to, wireless internet networks (WiFi™), Bluetooth®, or cellular networks. In these instances, the dental appliance may include a transmitter.

In some instances, the disclosed tooth repositioning systems (aligner change indicator systems) may comprise a means of communicating data from the aligner to a remote computer comprising a server and a processor which are linked. This remote computer may store and analyze the data. Data communication in these instances may be achieved using any of a variety of techniques and standards known to those of skill in the art including, but not limited to, wireless internet networks (WiFi™), Bluetooth®, or cellular networks. In these instances, the dental appliance may include a transmitter.

In the instances where the aligner communicates directly with a cell phone, the system may also allow the cell phone to communicate the data to the remote computer for data analysis and/or storage. Again this may be achieved using any of a variety of techniques and standards known to those of skill in the art including, but not limited to, wireless internet networks (WiFi™) Bluetooth®, or cellular networks. Such decentralization may make the data readily accessible to both the patient and the physician.

In the instances where the aligner communicates directly to the remote computer, the system may also allow the remote server to communicate the data to a cell phone, other computer, or other device for viewing by the patient and/or physician. This may be achieved using any of a variety of techniques and standards known to those of skill in the art including, but not limited to, wireless internet networks (WiFi™), Bluetooth®, or cellular networks. Such decentralization may make the data readily accessible to both the patient and the physician.

In some instances, two-way wireless communication between the dental appliance and a cell phone or remote processor may be used to transfer power or other data as well as sensor signal data.

Cell Phone App

In the case where the system includes a cell phone, the cell phone may include an application which is programmed specifically to communicate with the dental appliance, and if appropriate, the remote computer. The cell phone app will record the data from the dental appliance and make a determination as to whether it is time to change the dental appliance. This check may happen once per day, once per week, once per month, once every two months, or at any time interval included in these time intervals. The determination can be made based on the strain, the difference in strain from the last check, the positions of one or more teeth, the change in the position of one or more teeth compared to the last check, or any combination of these factors. The determination can be made based on the measurements from any number of teeth, at least one tooth and up to all of the teeth.

The appliance may be coupled to a different kind of device as well. Some examples for types of devices the appliance may communicate with that an app may be installed on include a personal computer, a cell phone, a tablet, and a smart watch or other wearable device. The app will provide the interface with which the patient and/or physician will interact with the data from the dental appliance. The app might provide an analysis of wear time, tooth movement trends, a history of tooth positions for the patient, an estimated timeline, an estimated treatment protocol, and a recommendation for a changing schedule for the series of dental appliances to be worn by the patient. The data may be analyzed on the device containing the app or remotely from the device. Some or all of this information may be derived from the data collected from the dental appliance, while some of this information may require input from the physician and/or patient. The recommendation for the changing schedule will be derived from the data collected from the dental appliance.

The determination as to whether it is time to change the dental appliance may depend on the movement of the teeth. This can be measured by measuring the strain on the appliance, which corresponds with the pressure the appliance puts on the teeth. Alternatively, this can be measured by measuring the movement of the teeth from their previous positions or toward their final positions. Alternatively, the time derivative of either of these measurements may be used to determine the changing schedule. The determination to change the dental appliance will be made when the teeth are in line with the dental appliance. In this case, the appliance will have already moved the teeth as far as it can. The dental appliance will no longer be exerting a significant repositioning force on the teeth.

The determination as to whether it is time to change the dental appliance may have, for example, three possible values: (1) change, (2) no action, and (3) too much strain/intervene. If the determination is no action, then no action will be taken, and no notification or message will be sent. The dental appliance will continue to measure the tooth movement, and the data will continue to be stored, analyzed, and/or transmitted until a different value is reached.

If the determination is being made based on a strain measurement, then the strain will be below a selected threshold, and the change in the strain over time will be below a selected threshold. If the determination is being made based on a tooth movement measurement, then the tooth position will be within a selected target range, and the change in tooth position over time will be below a selected threshold. Once the determination has been made that the dental appliance is no longer providing a significant repositioning force, it will alert the patient and/or the physician. This may be in the form of a push notification, text message, email, or other message or notification type.

If the dental appliance includes a sensor which indicates sensor wear, then each time the apparatus makes a strain or tooth position measurement, a check will be performed to determine if the dental appliance is currently being worn. If yes, then the process will proceed as described above. If no, then the data will not be recorded until the next check where the dental appliance is being worn. Alternatively, if the dental appliance is not being worn, the appliance can go into a standby mode, where no checks will be performed until the dental appliance is re-inserted into the mouth. If the dental appliance is not being worn for a minimum of a selected threshold number of hours per day, an alert may be sent to the physician indicating that the dental appliance is not being worn, and the treatment plan may be adjusted accordingly.

In some patients, the teeth will be moving too fast, or too much force may be applied to the teeth. If the determination is being made based on a strain measurement, then the strain will be above a selected threshold, and the change in strain over time will be above a selected threshold. If the determination is being made based on tooth movement measurement, then the tooth position will be outside a selected range, where the range is determined by how long the particular dental appliance has been in use, and the change in tooth position over time will be above a selected threshold. Once the determination has been made that the dental appliance is proving too much strain, including if it is providing a dangerous level of strain, an alert will be sent to the patient and/or physician. This may be in the form of a push notification, text message, email, or other message or notification type.

Once an alert is sent to the patient and/or physician, the physician can then make a final decision on the course of treatment based on the recorded data.

The present disclosure provides systems comprising one or more appliances comprising sensors, and an external processing device as described herein. The one or more dental repositioning appliances may comprise a removable polymeric shell aligner that includes tooth receiving cavities shaped to receive a patient tooth and apply a repositioning force to the tooth to move the tooth from a first position towards a second position. The appliance may comprise one or more sensors positioned adjacent to one or more teeth when the dental repositioning appliance is worn by the patient. The one or more sensors may be located on or in a buccal or lingual sidewall of a tooth receiving cavity for the appliance. The one or more sensors may be configured for wireless transmission of one or more signals generated by the one or more sensors to the external signal processing device. In some cases, the external signal processing device may be configured to calculate a corrective force vector or a rate of movement for the one or more teeth.

Data Processing and Fabrication System

Figure 6:
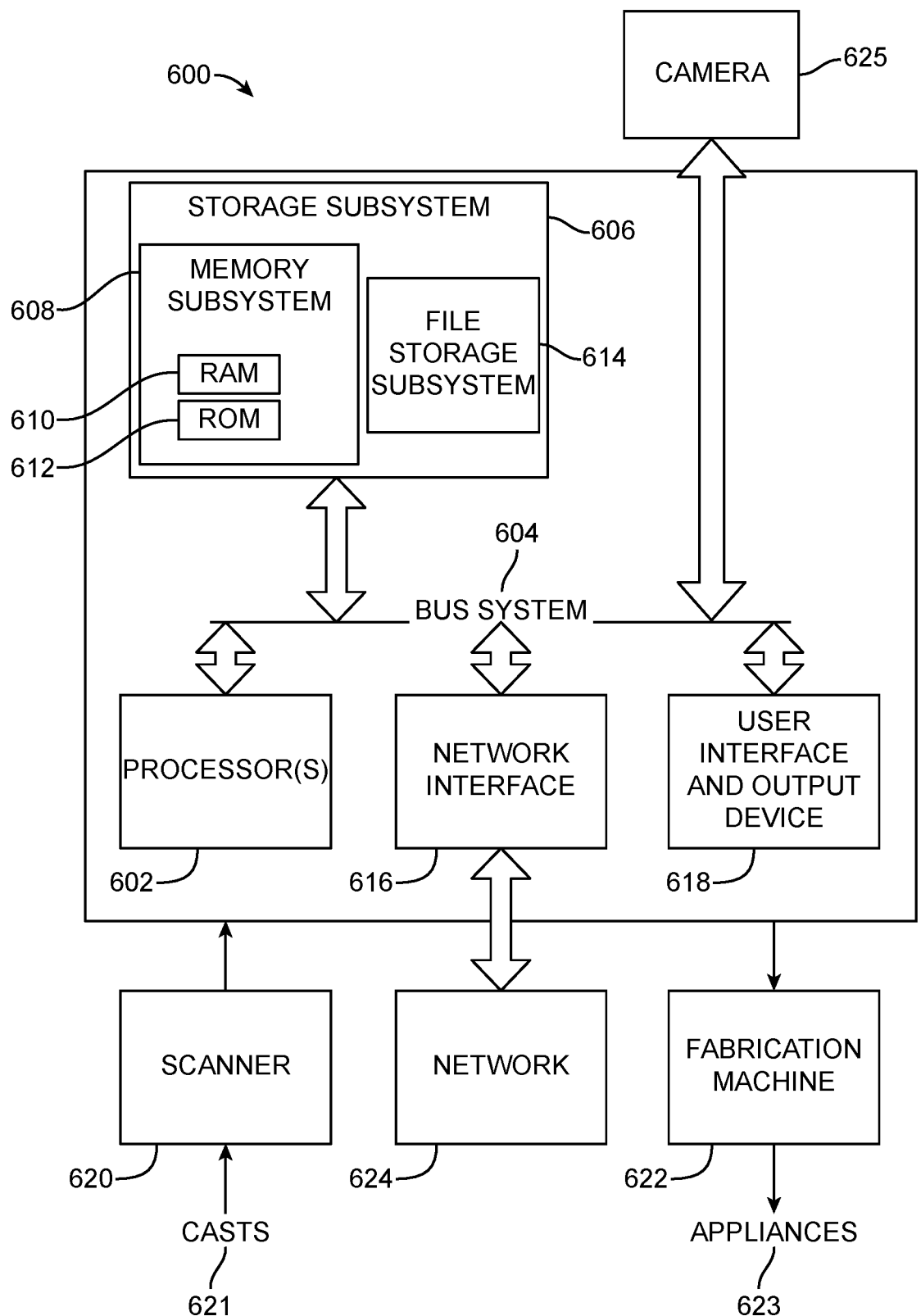
FIG. 6 is a simplified block diagram of a system for designing an orthodontic appliance and planning an orthodontic treatment, in accordance with one or more aspects of the methods, devices, and systems disclosed herein.

FIG. 6 is a simplified block diagram of a data processing system 600 that may be used in executing methods and processes described herein. The data processing system 600 typically includes at least one processor 602 that communicates with one or more peripheral devices via bus subsystem 604. These peripheral devices typically include a storage subsystem 606 (memory subsystem 608 and file storage subsystem 614), a set of user interface input and output devices 618, and an interface to outside networks 616. This interface is shown schematically as "Network Interface" block 616, and is coupled to corresponding interface devices in other data processing systems via communication network interface 624. Data processing system 600 can include, for example, one or more computers, such as a personal computer, workstation, mainframe, laptop, and the like.

The user interface input devices 618 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 606 maintains the basic required programming, including computer readable media having instructions (e.g., operating instructions, etc.), and data constructs. The program modules discussed herein are typically stored in storage subsystem 606. Storage subsystem 606 typically includes memory subsystem 608 and file storage subsystem 614. Memory subsystem 608 typically includes a number of memories (e.g., RAM 610, ROM 612, etc.) including computer readable memory for storage of fixed instructions, instructions and data during program execution, basic input/output system, etc. File storage subsystem 614 provides persistent (non-volatile) storage for program and data files, and can include one or more removable or fixed drives or media, hard disk, floppy disk, CD-ROM, DVD, optical drives, and the like. One or more of the storage systems, drives, etc., may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that may be known or recognized as suitable for use therein. It will be recognized that various components of the system can be, but need not necessarily be at the same physical location, but may be connected via various local-area or wide-area network media, transmission systems, etc.

Scanner 620 includes any means for obtaining a digital representation (e.g., images, surface topography data, etc.) of a patient's teeth (e.g., by scanning physical models of the teeth such as casts 621, by scanning impressions taken of the teeth, or by directly scanning the intraoral cavity), which can be obtained either from the patient or from treating professional, such as an orthodontist, and includes means of providing the digital representation to data processing system 600 for further processing. Scanner 620 may be located at a location remote with respect to other components of the system and can communicate image data and/or information to data processing system 600, for example, via a network interface 624. Fabrication system 622 fabricates appliances 623 based on a treatment plan, including data set information received from data processing system 600. Fabrication machine 622 can, for example, be located at a remote location and receive data set information from data processing system 600 via network interface 624. The camera 625 may include any image capture device configured to capture still images or movies. The camera 625 may facilitate capturing various perspectives of a patient's dentition. In some implementations, the camera 625 may facilitate capture of images at various focal lengths and distances from the patient.

The data processing aspects of the methods described herein can be implemented in digital electronic circuitry, or in computer hardware, firmware, software, or suitable combinations thereof. Data processing apparatus can be implemented in a computer program product tangibly embodied in a machine-readable storage device for execution by a programmable processor. Data processing blocks can be performed by a programmable processor executing program instructions to perform functions by operating on input data and generating output. The data processing aspects can be implemented in one or more computer programs that are executable on a programmable system, the system including one or more programmable processors operably coupled to a data storage system. Generally, a processor will receive instructions and data from a read-only memory and/or a random access memory. Storage devices suitable for tangibly embodying computer program instructions and data include all forms of nonvolatile memory, such as: semiconductor memory devices, such as EPROM, EEPROM, and flash memory devices; magnetic disks such as internal hard disks and removable disks; magneto-optical disks; and CD-ROM disks.

It is within the scope of the present disclosure to use sensors for determining progress of treatment on other orthodontic devices such as palatal expanders, MAFT devices, jaw movements, or other treatments that involve progressive iterations of treatment with devices.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
sensing a first physical quality of a first region of a first aligner, the first aligner comprising a polymeric shell and an intersecting array of microfluidic channels embedded within the polymer shell,
wherein the first aligner is configured to move one or more teeth in accordance with a first stage of a treatment plan,
wherein the first physical quality corresponds to a spatially distributed strain in the polymeric shell of the first aligner,
wherein the first region corresponds to a location in the intersecting array of microfluidic channels, and
wherein the sensing of the first physical quality of the first region of the first aligner is executed at least in part by measuring a capacitance between two or more channels of the intersection array of microfluidic channels coupled to the first region of the first aligner;
identifying a value for the first physical quality based on the measured capacitance;
making a first determination whether the value of the first physical quality is less than a threshold value, the threshold value corresponding to a specified reduction in a force applied by the polymeric shell to the one or more teeth in accordance with the first stage of the treatment plan; and
providing a signal representative of the first determination.

2. The method of claim 1, wherein the signal comprises an electrical signal.

3. The method of claim 1, further comprising sensing a movement of the first region of the first aligner based at least in part on a change in electrical conductivity based on the sensed movement.

4. The method of claim 1, wherein the first physical quality is sensed at least in part by a plurality of sensor legs configured to sense a distance between two more of the plurality of sensor legs.

5. The method of claim 1, wherein the threshold value is associated with a relaxation of a first aligner material of the first aligner beyond a relaxation threshold.

6. The method of claim 5, wherein the first aligner material comprises a thermoformed multilayer sheet.

7. The method of claim 5, wherein the first aligner material comprises a lithography-based photo polymerized resin.

8. The method of claim 1, further comprising:
identifying in the treatment plan a prescribed time for the first aligner;
identifying, based on the first determination, an effective time of the first aligner, the effective time associated with the specified reduction in force; and
determining, based on a comparison of the effective time and the prescribed time, whether or not to use the prescribed time for the first aligner.

9. The method of claim 8, further comprising providing a recommendation to accelerate implementation of a second aligner used to move the one or more teeth in accordance with a second stage of the treatment plan if the effective time of the first aligner is less than the prescribed time.

10. The method of claim 8, further comprising providing a recommendation to decelerate implementation of a second aligner used to move the one or more teeth in accordance with a second stage of the treatment plan if the effective time of the first aligner is greater than the prescribed time.

11. The method of claim 1, wherein the first region corresponds to a leading tooth of the one or more teeth.

12. The method of claim 1, further comprising using the value of the first physical quality to identify a presence or absence of a repositioning force sufficient to move the one or more teeth.

13. The method of claim 12, wherein using the value of the first physical quality comprises:
calculating a change of the value of the first physical quality over an amount of time, and
comparing the change to a maximum amount of change in strain for the first aligner to be effective.

14. The method of claim 13, further comprising:
calculating, for each of the one or more teeth, a change in a corresponding spatially distributed strain in a corresponding subregion of the polymeric shell over the amount of time, and
comparing the changes in the corresponding spatially distributed strains to a respective maximum amount of change in strain for the first aligner to be effective.

15. The method of claim 14, further comprising calculating an average of the changes of the corresponding spatially distributed strains of a subset of the one or more teeth.

16. The method of claim 14, further comprising calculating an average of the changes of the corresponding spatially distributed strains of all of the one or more teeth.

17. The method of claim 1, further comprising tracking a position of one of the one or more teeth relative to another of the one or more teeth over time to determine a movement rate.

18. The method of claim 1, further comprising calculating a corrective force vector based at least in part on the value of the first physical quality.

19. The method of claim 1, further comprising:
sensing one or more second physical qualities that indicate a patient's compliance with wearing of the first aligner; and
providing a recommendation to accelerate or decelerate implementation of a second aligner of the treatment plan based on the first physical quality and on the one or more second physical qualities.

20. The method of claim 1, further comprising:
sensing a second physical quality of a second region of the first aligner that is different from the first region; and
providing a recommendation to accelerate or decelerate implementation of a second aligner of the treatment plan based at least in part on the first physical quality of the first region and the second physical quality of the second region.

* * * * *